United States Patent
Swanson et al.

(10) Patent No.: US 10,668,148 B2
(45) Date of Patent: Jun. 2, 2020

(54) FULLY HUMAN ANTI-C-X-C CHEMOKINE RECEPTOR 3 (CXCR3) ANTIBODIES AND METHODS OF USE THEREOF

(71) Applicant: Sorrento Therapeutics, Inc., San Diego, CA (US)

(72) Inventors: Barbara A. Swanson, Encinitas, CA (US); Dingqiu Huang, San Diego, CA (US); Heyue Zhou, San Diego, CA (US)

(73) Assignee: Sorrento Therapeutics. inc., San Diego, CA (US)

( * ) Notice: Subject to any disclaimer, the term of this patent is extended or adjusted under 35 U.S.C. 154(b) by 0 days.

(21) Appl. No.: 16/155,278

(22) Filed: Oct. 9, 2018

(65) Prior Publication Data

US 2019/0060448 A1    Feb. 28, 2019

Related U.S. Application Data

(62) Division of application No. 15/682,206, filed on Aug. 21, 2017, now abandoned, which is a division of application No. 14/821,559, filed on Aug. 7, 2015, now Pat. No. 9,765,145.

(60) Provisional application No. 62/041,020, filed on Aug. 22, 2014.

(51) Int. Cl.
  *A61K 39/395* (2006.01)
  *C07K 16/28* (2006.01)

(52) U.S. Cl.
  CPC ........ *A61K 39/395* (2013.01); *C07K 16/2809* (2013.01); *C07K 16/2866* (2013.01); *C07K 2317/21* (2013.01); *C07K 2317/76* (2013.01); *C07K 2317/92* (2013.01)

(58) Field of Classification Search
  CPC ............ A61K 39/395; A61K 2039/505; C07K 16/2809; C07K 16/2866; C07K 2317/21; C07K 2317/55; C07K 2317/76; C07K 2317/92
  See application file for complete search history.

(56) References Cited

U.S. PATENT DOCUMENTS

| | | |
|---|---|---|
| 2010/0254975 A1 | 10/2010 | Hsu et al. |
| 2011/0280875 A1 | 11/2011 | Qin et al. |
| 2013/0251733 A1 | 9/2013 | Youd et al. |

OTHER PUBLICATIONS

International Search Report and Written Opinion for PCT/US2015/044348 dated Jun. 9, 2016.
Paul, WE. Fundamental Immunology, 3rd ed. Raven Press, NY, Chap. 9, pp. 292-295, 1993.
Rudikoff S. et al. Proc. Natl. Acad. Sci. USA, 79:1979-1983, 1982.
Colman, PM. Research in Immunology, Elsevier, NY, 145(1):33-36, 1994.

*Primary Examiner* — Robert S Landsman
(74) *Attorney, Agent, or Firm* — McNeill Baur PLLC

(57) ABSTRACT

There is disclosed compositions and methods relating to or derived from anti-CXCR3 antibodies. More specifically, there is disclosed fully human antibodies that bind CXCR3, CXCR3-binding fragments and derivatives of such antibodies, and CXCR3-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having CXCR3 related disorders or conditions, including various inflammatory disorders and various cancers.

14 Claims, 1 Drawing Sheet
Specification includes a Sequence Listing.

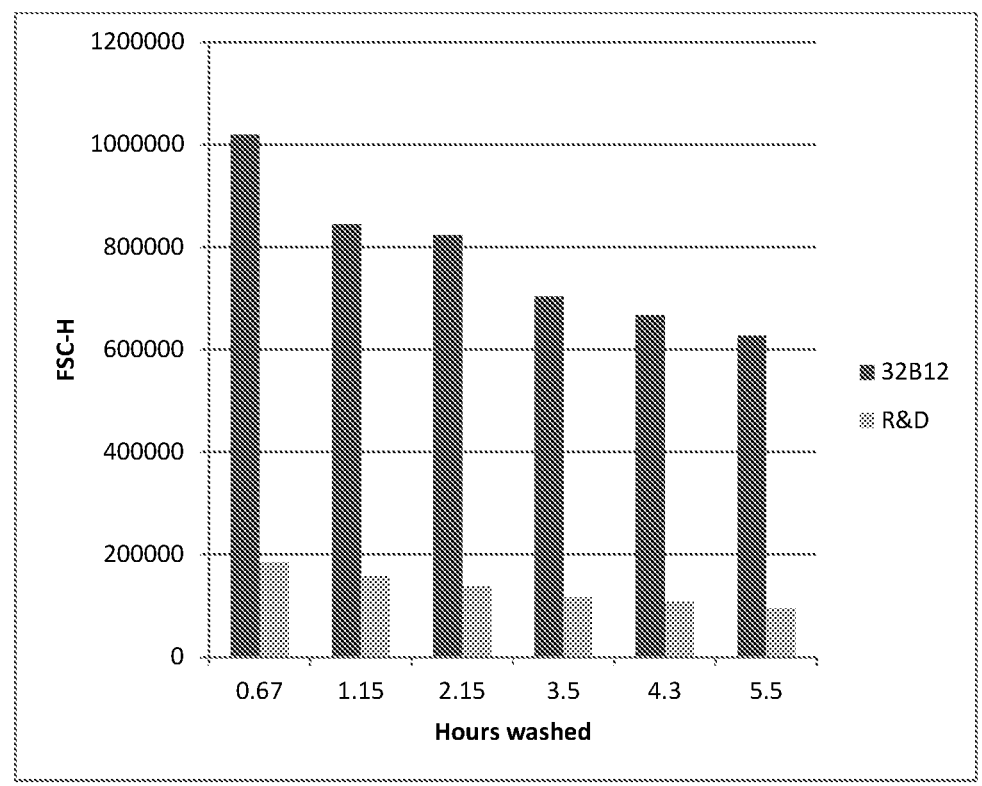

FULLY HUMAN ANTI-C-X-C CHEMOKINE RECEPTOR 3 (CXCR3) ANTIBODIES AND METHODS OF USE THEREOF

PRIORITY APPLICATIONS

This patent application is a divisional of U.S. patent application Ser. No. 15/682,206 filed on Aug. 21, 2017, which is a divisional of U.S. patent application Ser. No. 14/821,559, filed on Aug. 7, 2015, now U.S. Pat. No. 9,765,145 and which claims the benefit of priority from U.S. provisional patent application Ser. No. 62/041,020 filed 22 Aug. 2015. The entire contents of the foregoing are incorporated herein by reference.

The instant application contains a Sequence Listing which has been submitted in ASCII format via EFS-Web and is hereby incorporated by reference in its entirety. Said ASCII copy, created on Oct. 9, 2018, is named S103014 1220 US D2.txt and is 44 kilobytes in size.

TECHNICAL FIELD

The present disclosure provides compositions and methods relating to or derived from anti-CXCR3 antibodies. More specifically, the present disclosure provides human antibodies that bind CXCR3, CXCR3-binding fragments and derivatives of such fragments, and CXCR3-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having CXCR3 related disorders or conditions, including various inflammatory disorders and various cancers.

BACKGROUND

C-X-C chemokine receptor-3 (CXCR3) is expressed on certain leukocytes, such as activated T cells and NK cells. The CXCR3 receptor binds ligands, such as Interferon Gamma-inducible 10 kD Protein (IP-10), Monokine Induced by Gamma interferon (MIG; Mig), Interferon-inducible T-cell Alpha Chemoattractant (I-TAC) and B cell-attracting chemokine-1 (BCA-1). Certain forms of CXCR3 also bind platelet factor-4 (PF-4, Lasagni et al., *J. Exp. Med.* 197: 1537-1549, 2003). The expression of some of the CXCR3 ligands (IP-10, MIG and I-TAC), is induced in tissues by inteferons or Tumor Necrosis Factor (TNF), potent mediators of inflammation (Farber, J. M. *J. Leukoc. Biol.* 61:246-257, 2007; Piali, et al. *Eur. J. Immunol.* 28:961-972, 1998; and Cole et al. *J. Exp. Med.* 187:2009-2021, 1998). Because of these findings, it has been postulated that during inflammation, expression of ligands for CXCR3 is upregulated, resulting in recruitment of CXCR3+ lymphocytes into the inflamed tissue. The infiltrating CXCR3+ lymphocytes can contribute to adverse pathological effects of inflammation. Inhibiting the activities of CXCR3, therefore, can have beneficial anti-inflammatory effects. Therefore, there is a need for therapeutic agents that inhibit CXCR3 function.

The interaction between chemokines and their receptors is an important step in the control of leukocyte migration. Chemokines also mediate a variety of effects independent of chemotaxis, including induction and enhancement of cell-associated cytokine responses.

The human cell surface protein CD183 is a G protein-coupled receptor with selectivity for three chemokines including IP10 (interferon-γ-inducible 10 kDa protein), Mig (monokine induced by interferon-γ) and I-TAC (interferon-inducible T cell α-chemoattractant). These three chemokines belong to the structural subfamily of "CXC" chemokines, in which a single amino acid residue separates the first two of four highly conserved Cys residues. Historically, CD183 is the third CXC chemokine receptor discovered and, therefore, CD183 is commonly designated as "CXCR3." Binding of chemokines to CXCR3 induces cellular responses that are involved in leukocyte traffic, most notably integrin activation, cytoskeletal changes and chemotactic migration. CXCR3 is expressed on effector/memory T cells and/or in T cells present in many types of inflamed tissues (e.g., T-helper 1 cells or Th1 cells and CD8+ Tc1 cells). In addition, IP10, Mig and I-TAC are commonly produced by local cells in inflammatory lesions, suggesting that CXCR3 and its chemokines participate in the recruitment of white blood cells to sites of inflammation. Therefore, CXCR3 is a target for the development of antibodies and antagonists, which may be used in the treatment and diagnosis of diverse inflammatory and immune diseases and disorders, such as rheumatoid arthritis, multiple sclerosis, Crohn's disease, inflammatory bowel disease, chronic obstructive pulmonary disease, psoriasis, type 1 diabetes and transplant rejection. Because CXCR3 is expressed on a subset of B-cell lymphomas, CXCR3 may also be a target for treating and diagnosing lymphomas and leukemias.

Therefore, there is a need in the art for an improved anti-CXCR3 antibodies that can be used as therapeutic agents.

SUMMARY

The present disclosure provides a fully human antibody of an IgG class that binds to an CXCR3 epitope with a binding affinity of at least $10^{-6}$ M, which has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called 32B12 herein), SEQ ID NO. 3/SEQ ID NO. 4 (called 32D12 herein), SEQ ID NO. 5/SEQ ID NO. 6 (called H1 herein), SEQ ID NO. 7/SEQ ID NO. 8 (called B7 herein), SEQ ID NO. 9/SEQ ID NO. 10 (called C12 herein), SEQ ID NO. 1.11/SEQ ID NO. 12 (called D12 herein), SEQ ID NO. 13/SEQ ID NO. 14 (called E1 herein), SEQ ID NO. 15/SEQ ID NO. 16 (called G12 herein), SEQ ID NO. 17/SEQ ID NO. 18 (called 3A3 herein), SEQ ID NO. 19/SEQ ID NO. 20 (called 3A5 herein), SEQ ID NO. 21/SEQ ID NO. 22

(called 3A11 herein), SEQ ID NO. 23/SEQ ID NO. 24 (called 3B12 herein), SEQ ID NO. 25/SEQ ID NO.26 (called 3C11 herein), SEQ ID NO. 27/SEQ ID NO. 28 (called 4C3 herein), SEQ ID NO. 29/SEQ ID NO. 30 (called B12 herein), SEQ ID NO. 31/SEQ ID NO. 32 (called C4 herein), SEQ ID NO. 31/SEQ ID NO. 33 (called F7 herein), SEQ ID NO. 31/SEQ ID NO. 34 (called 2A3 herein), SEQ ID NO. 31/SEQ ID NO. 35 (called 3A7 herein), SEQ ID NO. 31/SEQ ID NO. 36 (called 3A8 herein), SEQ ID NO. 31/SEQ ID NO. 37 (called 4D5 herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof. Preferably, the fully human antibody Fab fragment has both a heavy chain variable domain region and a light chain variable domain region wherein the antibody has a heavy chain/light chain variable domain sequence selected from the group consisting SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 31/SEQ ID NO. 33, SEQ ID NO. 31/SEQ ID NO. 34, SEQ ID NO. 31/SEQ ID NO. 35, SEQ ID NO. 31/SEQ ID NO. 36, SEQ ID NO. 31/SEQ ID NO. 37, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1. SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 1.9/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 31/SEQ ID NO. 33, SEQ ID NO. 31/SEQ ID NO. 34, SEQ ID NO. 31.SEQ ID NO. 35, SEQ ID NO. 31/SEQ ID NO. 36, SEQ ID NO. 31/SEQ ID NO. 37, and combinations thereof.

The present disclosure further provides a method for treating a broad spectrum of mammalian cancers, comprising administering an effective amount of an anti-CXCR3 polypeptide, wherein the anti-CXCR3 polypeptide is selected from the group consisting of a fully human antibody of an IgG class that binds to a CXCR3 epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof; and wherein the single chain human antibody has the heavy chain variable domain sequence that is at least 95% identical to the amino acid sequences selected from the group consisting of SEQ ID NO. 1. SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17. SEQ ID NO. 19. SEQ ID NO. 21. SEQ ID NO. 23, SEQ ID NO. 25, SEQ ID NO. 27, SEQ ID NO. 29, SEQ ID NO. 31, SEQ ID NO. 33, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof.

Preferably, the fully human antibody has both a heavy chain and a light chain wherein the antibody has a heavy chain/light chain variable domain sequence selected from the group consisting SEQ ID NO. 1/SEQ ID NO. 2 (called 32B12 herein), SEQ ID NO. 3/SEQ ID NO. 4 (called 32D12 herein), SEQ ID NO. 5/SEQ ID NO. 6 (called H1 herein), SEQ ID NO. 7/SEQ ID NO. 8 (called B7 herein), SEQ ID NO. 9/SEQ ID NO. 10 (called C12 herein), SEQ ID NO. 11.SEQ ID NO. 12 (called D12 herein), SEQ ID NO. 13/SEQ ID NO. 14 (called E1 herein), SEQ ID NO. 15/SEQ ID NO. 16 (called G12 herein), SEQ ID NO. 17/SEQ ID NO. 18 (called 3A3 herein), SEQ ID NO. 19/SEQ ID NO. 20 (called 3A5 herein), SEQ ID NO. 21/SEQ ID NO. 22 (called 3A11 herein), SEQ ID NO. 23/SEQ ID NO. 24 (called 3B12 herein), SEQ ID NO. 25/SEQ ID NO.26 (called 3C11 herein), SEQ ID NO. 27/SEQ ID NO. 28 (called 4C3 herein), SEQ ID NO. 29/SEQ ID NO. 30 (called B12 herein). SEQ ID NO. 31/SEQ ID NO. 32 (called C4 herein), SEQ ID NO. 31/SEQ ID NO. 33 (called F7 herein), SEQ ID NO. 31/SEQ ID NO. 34 (called 2A3 herein), SEQ NO. 31/SEQ ID NO. 35 (called 3A7 herein), SEQ ID NO. 31/SEQ ID NO. 36 (called 3A8 herein), SEQ ID NO. 31/SEQ ID NO. 37 (called 4D5 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called 32B12 herein), SEQ ID NO. 3/SEQ ID NO. 4 (called 32D12 herein), SEQ ID NO. 5/SEQ ID NO. 6 (called H1 herein), SEQ ID NO. 7/SEQ ID NO. 8 (called B7 herein), SEQ ID NO. 9/SEQ ID NO. 10 (called C12 herein), SEQ ID NO. 11/SEQ ID NO. 12 (called D12 herein), SEQ ID NO. 13/SEQ ID NO. 14 (called E1 herein), SEQ ID NO. 15/SEQ ID NO. 16 (called G12 herein), SEQ ID NO. 17/SEQ ID NO. 18 (called 3A3 herein), SEQ ID NO. 19/SEQ ID NO. 20 (called 3A5 herein), SEQ ID NO. 21/SEQ ID NO. 22 (called 3A11 herein), SEQ ID NO. 23/SEQ ID NO. 24 (called 3B12 herein), SEQ ID NO. 25/SEQ ID NO.26 (called 3C11 herein), SEQ ID NO. 27/SEQ ID NO. 28 (called 4C3 herein), SEQ ID NO. 29/SEQ ID NO. 30 (called B12 herein), SEQ ID NO. 31/SEQ ID NO. 32 (called C4 herein), SEQ ID NO. 31/SEQ ID NO. 33 (called F7 herein), SEQ ID NO. 31/SEQ ID NO. 34 (called 2A3 herein), SEQ ID NO. 31/SEQ ID NO. 35 (called 3A7 herein), SEQ ID NO. 31/SEQ ID NO. 36 (called 3A8 herein), SEQ ID NO. 31/SEQ ID NO. 37 (called 4D5 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 31/SEQ ID NO. 33, SEQ ID NO. 31/SEQ ID NO. 34, SEQ ID NO. 31/SEQ ID NO. 35, SEQ ID NO. 31/SEQ ID NO. 36, SEQ ID NO. 31/SEQ ID NO. 37, and combinations thereof.

Preferably, the broad spectrum of mammalian cancers to be treated the cancer is a CXCR3-positive cancer. Preferably, the broad spectrum of mammalian cancers to be treated is selected from the group consisting of leukemias, lymphomas, carcinomas, prostate cancer, non-small cell lung cancer, breast cancer, endometrial cancer, ovarian cancer, gastric cancers, head and neck cancers, melanoma, osteosarcoma, intestinal and colon cancer, and various metastatic cancers.

The present disclosure further provides a method for treating an inflammatory disorders, comprising administering an effective amount of an anti-CXCR3 polypeptide, wherein the anti-CXCR3 polypeptide is selected from the group consisting of a fully human antibody of an IgG class that hinds to a CXCR3 epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. SEQ ID NO. 33, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17. SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof.

Preferably, the fully human antibody has both a heavy chain and a light chain wherein the antibody has a heavy chain/light chain variable domain sequence selected from the group consisting SEQ ID NO. 1/SEQ ID NO. 2 (called 32B12 herein), SEQ ID NO. 3/SEQ ID NO. 4 (called 32D12 herein), SEQ ID NO. 5/SEQ ID NO. 6 (called H1 herein), SEQ ID NO. 7/SEQ ID NO. 8 (called B7 herein), SEQ ID NO. 9/SEQ ID NO. 10 (called C12 herein), SEQ ID NO. 11/SEQ ID NO. 12 (called D12 herein), SEQ ID NO. 13/SEQ ID NO. 14 (called E1 herein), SEQ ID NO. 15/SEQ ID NO. 16 (called G12 herein), SEQ ID NO. 17/SEQ ID NO. 18 (called 3A3 herein), SEQ ID NO. 19/SEQ ID NO. 20 (called 3A5 herein), SEQ ID NO. 21/SEQ ID NO. 22 (called 3A11 herein), SEQ ID NO. 23/SEQ ID NO. 24 (called 3D12 herein), SEQ ID NO. 25/SEQ ID NO.26 (called 3C11 herein), SEQ ID NO. 27/SEQ ID NO. 28 (called 4C3 herein), SEQ ID NO. 29/SEQ ID NO. 30 (called B12 herein), SEQ ID NO. 31/SEQ ID NO. 32 (called C4 herein), SEQ ID NO. 31/SEQ ID NO. 33 (called F7 herein), SEQ ID NO. 31/SEQ ID NO. 34 (called 2A3 herein), SEQ ID NO. 31/SEQ ID NO. 35 (called 3A7 herein), SEQ ID NO. 31/SEQ ID NO. 36 (called 3A8 herein), SEQ ID NO. 31/SEQ ID NO. 37 (called 4D5 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called 32B12 herein), SEQ ID NO. 3/SEQ ID NO. 4 (called 32D12 herein), SEQ ID NO. 5/SEQ ID NO. 6 (called H1 herein), SEQ ID NO. 7/SEQ ID NO. 8 (called B7 herein), SEQ ID NO. 9/SEQ ID NO. 10 (called C12 herein), SEQ ID NO. 11/SEQ ID NO. 12 (called D12 herein), SEQ ID NO. 13/SEQ ID NO. 14 (called E1 herein), SEQ ID NO. 15/SEQ ID NO. 16 (called G12 herein), SEQ ID NO. 17/SEQ ID NO. 18 (called 3A3 herein), SEQ ID NO. 19/SEQ ID NO. 20 (called 3A5 herein), SEQ ID NO. 21/SEQ ID NO. 22 (called 3A11 herein), SEQ ID NO. 23/SEQ ID NO. 24 (called 3D12 herein), SEQ ID NO. 25/SEQ ID NO.26 (called 3C11 herein), SEQ ID NO. 27/SEQ ID NO. 28 (called 4C3 herein), SEQ ID NO. 29/SEQ ID NO. 30 (called B12 herein), SEQ ID NO. 31/SEQ ID NO. 32 (called C4 herein), SEQ ID NO. 31/SEQ ID NO. 33 (called F7 herein), SEQ ID NO. 31/SEQ ID NO. 34 (called 2A3 herein), SEQ ID NO. 31/SEQ ID NO. 35 (called 3A7 herein), SEQ ID NO. 31/SEQ ID NO. 36 (called 3A8 herein), SEQ ID NO. 31/SEQ ID NO. 37 (called 4D5 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 31/SEQ ID NO. 33, SEQ ID NO. 31/SEQ ID NO. 34, SEQ ID NO. 31/SEQ ID NO. 35, SEQ ID NO. 31/SEQ ID NO. 36, SEQ ID NO. 31/SEQ ID NO. 37, and combinations thereof.

Preferably, the inflammatory disorder to be treated is selected from the group consisting of rheumatoid arthritis, multiple sclerosis, Crohn's disease, Graves disease, Sjögren's syndrome, inflammatory bowel disease, chronic obstructive pulmonary disease, psoriasis, type 1 diabetes, transplant rejection chronic hepatitis C, malaria, and atherosclerosis.

BRIEF DESCRIPTION OF THE FIGURES

FIG. 1 shows binding of the anti-CXCR3 antibody 32B12 to CHO-CXCR3 cells.

DETAILED DESCRIPTION

The present disclosure provides a fully human antibody of an IgG class that binds to a CXCR3 epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof. Preferably, the fully human antibody has both a heavy chain and a light chain wherein the antibody has a heavy chain/ light chain variable domain sequence selected from the group consisting of SEQ ID NO. 1/SEQ ID NO. 2 (called 32B12 herein), SEQ ID NO. 3/SEQ ID NO. 4 (called 32D12 herein), SEQ ID NO. 5/SEQ ID NO. 6 (called H1 herein), SEQ ID NO. 7/SEQ ID NO. 8 (called B7 herein), SEQ ID NO. 9/SEQ ID NO. 10 (called C12 herein), SEQ ID NO.

11/SEQ ID NO. 12 (called D12 herein), SEQ ID NO. 13/SEQ ID NO. 14 (called E1 herein), SEQ ID NO. 15/SEQ ID NO. 16 (called G12 herein), SEQ ID NO. 17/SEQ ID NO. 18 (called 3A3 herein), SEQ ID NO. 19/SEQ ID NO. 20 (called 3A5 herein), SEQ ID NO. 21/SEQ ID NO. 22 (called 3A11 herein), SEQ ID NO. 23/SEQ ID NO. 24 (called 3B12 herein), SEQ ID NO. 25/SEQ ID NO.26 (called 3C11 herein), SEQ ID NO. 27/SEQ ID NO. 28 (called 4C3 herein), SEQ ID NO. 29/SEQ ID NO. 30 (called B12 herein), SEQ ID NO. 31/SEQ ID NO. 32 (called C4 herein), SEQ ID NO. 31/SEQ ID NO. 33 (called F7 herein), SEQ ID NO. 31/SEQ ID NO. 34 (called 2A3 herein), SEQ ID NO. 31/SEQ ID NO. 35 (called 3A7 herein), SEQ ID NO. 31/SEQ ID NO. 36 (called 3A8 herein), SEQ ID NO. 31/SEQ ID NO. 37 (called 4D5 herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 31/SEQ ID NO. 33, SEQ ID NO. 31/SEQ ID NO. 34, SEQ ID NO. 31/SEQ ID NO. 35, SEQ ID NO. 31/SEQ ID NO. 36, SEQ ID NO. 31/SEQ ID NO. 37, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 31/SEQ ID NO. 33, SEQ ID NO. 31/SEQ ID NO. 34, SEQ ID NO. 31/SEQ ID NO. 35, SEQ ID NO. 31/SEQ ID NO. 36, SEQ ID NO. 31/SEQ ID NO. 37, and combinations thereof.

The present disclosure further provides a method for treating a broad spectrum of mammalian cancers or inflammatory diseases or autoimmune diseases, comprising administering an effective amount of an anti-CXCR3 polypeptide, wherein the anti-CXCR3 polypeptide is selected from the group consisting of a fully human antibody of an IgG class that binds to a CXCR3 epitope with a binding affinity of at least $10^{-6}$K a fully human antibody Fab fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 33, SEQ ID NO. 34, SEQ ID NO. 35, SEQ ID NO. 36, SEQ ID NO. 37, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20. SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 31/SEQ ID NO. 33, SEQ ID NO. 31/SEQ ID NO. 34, SEQ ID NO. 31/SEQ ID NO. 35, SEQ ID NO. 31/SEQ ID NO. 36, SEQ ID NO. 31/SEQ ID NO. 37, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 31/SEQ ID NO. 33, SEQ ID NO. 31/SEQ ID NO. 34, SEQ ID NO. 31/SEQ ID NO. 35, SEQ ID NO. 31/SEQ ID NO. 36, SEQ ID NO. 31/SEQ ID NO. 37, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 31/SEQ ID NO. 33, SEQ ID NO. 31/SEQ ID NO. 34. SEQ ID NO. 31/SEQ ID NO. 35, SEQ ID NO. 31/SEQ ID NO. 36, SEQ ID NO. 31/SEQ ID NO. 37, and combinations thereof.

Preferably, the broad spectrum of mammalian cancers to be treated the cancer is a CXCR3-positive cancer. Preferably, the broad spectrum of mammalian cancers to be treated is selected from the group consisting of leukemias, lymphomas, carcinomas, prostate cancer, non-small cell lung cancer, breast cancer, endometrial cancer, ovarian cancer, gastric cancers, head and neck cancers, melanoma, osteosarcoma, intestinal and colon cancer, and various metastatic cancers. Preferably, the inflammatory disorder to be treated is selected from the group consisting of rheumatoid arthritis, multiple sclerosis, Crohn's disease, Graves' disease, Sjögren's syndrome, inflammatory bowel disease, chronic obstructive pulmonary disease, psoriasis, type 1 diabetes, transplant rejection chronic hepatitis C, malaria, and atherosclerosis.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hyper variable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, J. Mol. Biol. 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or VL domain (U.S. Pat. Nos. 6,846,634; 6,696,245, US Patent Applications 2002/02512; 2004/0202995; 2004/0038291; 2004/0009507; 2003/0039958, and Ward et al., *Nature* 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (Holliger et al., *Proc. Natl. Acad. Sci. USA* 90:6444-48, 1993 and Poljak et al., *Structure* 2:1121-23, 1994). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-CXCR3 antibody. In another embodiment, all of the CDRs are derived from a human anti-CXCR3 antibody. In another embodiment, the CDRs from more than one human anti-CXCR3 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-CXCR3 antibody, and the CDRs from the heavy chain from a third anti-CXCR3 antibody. Other combinations are possible.

Further, the framework regions may be derived from one of the same anti-CXCR3 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind CXCR3).

A "neutralizing antibody" or an "inhibitory antibody" is an antibody that inhibits the activation of CXCR3 when an excess of the anti-CXCR3 antibody reduces the amount of activation by at least about 20% using an assay such as those described herein in the Examples. In various embodiments, the antigen binding protein reduces the amount of amount of activation of CXCR3 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CXCR3) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, mutation or environmental influence, such progeny may not, in fact, be identical to the parent cell, but are still included within the scope of the term as used herein.

Preferably, the mammalian cancer to be treated is selected from the group consisting of ovarian, colon, breast or hepatic carcinoma cell lines, myelomas, neuroblastic-derived CNS tumors, monocytic leukemias, B-cell derived leukemia's, T-cell derived leukemias, B-cell derived lymphomas, T-cell derived lymphomas, mast cell derived tumors, and combinations thereof.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

CXCR3-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one specific embodiment, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. No. 4,640,835; 1,496,689; 4,301,144; 4,670,417; 4,791,192 or 4,179,337. Examples of the modified polypeptide include PEGylated antibodies.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$-1CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

Although PEG is well-known, this is the first demonstration that a pegylated$^{10F}$n3 polypeptide can be pegylated and retain ligand binding activity. In a preferred embodiment, the pegylated$^{10F}$nF peptide is produced by site-directed pegylation, particularly by conjugation of PEG to a cysteine moiety at the N- or C-terminus. Accordingly, the present disclosure provides a target-binding $^{10F}$nF polypeptide with improved pharmacokinetic properties, the polypeptide comprising: a $^{10F}$nF domain having from about 80 to about 150 amino acids, wherein at least one of the loops of said $^{10F}$n3 domain participate in target binding; and a covalently bound PEG moiety, wherein said $^{10F}$n3 polypeptide binds to the target with a K$_D$ of less than 100 nM and has a clearance rate of less than 30 mL/hr/kg in a mammal. The PEG moiety may be attached to the $^{10F}$n3 polypeptide by site directed pegylation, such as by attachment to a Cys residue, where the Cys residue may be positioned at the N-terminus of the $^{0F}$n3 polypeptide or between the N-terminus and the most N-terminal beta or beta-like strand or at the C-terminus of the $^{10F}$n3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., *J. Biol. Chem.,* 252, 3571 (1977) and *J. Biol. Chem.,* 252, 3582 (1977), Zalipsky, et al., and Hank et. al., in: *Poly(ethylene glycol) Chemistry: Biotechnical and Biomedical Applications*; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

A variety of molecular mass forms of PEG can be selected, e.g., from about 1,000 Daltons (Da) to 100,000 Da (n is 20 to 2300), for conjugating to CXCR3-binding polypeptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820) the molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the disclosure an CXCR3 binding polypeptide is covalently linked to one poly(ethylene glycol) group of the formula: —CO—(CH$_2$)$_x$—(OCH$_2$CH$_2$)$_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's ϵ-amino group of a lysine is the available (free) amino group.

The above conjugates may be more specifically presented by formula (II): P—NHCO—$(CH_2)_x$—$(OCH_2CH_2)_m$—OR (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group.

One skilled in the art can select a suitable molecular mass for PEG, e.g., based on how the pegylated binding polypeptide will be used therapeutically, the desired dosage, circulation time, resistance to proteolysis, immunogenicity, and other considerations. For a discussion of PEG and its use to enhance the properties of proteins, see Katre, *Advanced Drug Delivery Reviews* 10: 91-114 (1993).

In one embodiment, PEG molecules may be activated to react with amino groups on a binding polypeptide, such as with lysines (Bencham et al., *Anal. Biochem.*, 131, 25 (1983); Veronese et al., *Appl. Biochem.*, 11, 141 (1985); Zalipsky et al., *Polymeric Drugs and Drug Delivery Systems*, adrs 9-110 ACS Symposium Series 469 (1999); Zalipsky et al., *Europ. Polym. J.*, 19, 1177-1183 (1983); Delgado et al., *Biotechnology and Applied Biochemistry*, 12, 119-128 (1990)).

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. Nos. 5,281,698 and 5,932,462). In a similar type of reaction, 1,1'-(dibenzotriazolyl)carbonate and di-(2-pyridyl) carbonate may be reacted with PEG to form PEG-benzotriazolyl and PEG-pyridyl mixed carbonate (U.S. Pat. No. 5,382,657), respectively.

Pegylation of a $^{10F}$n3 polypeptide can be performed according to the methods of the state of the art, for example by reaction of the binding polypeptide with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini et al., *Bioconjugate Chem.* 6 (1995) 62-69). Such methods may be used to pegylated at an ϵ-amino group of a binding polypeptide lysine or the N-terminal amino group of the binding polypeptide.

In another embodiment, PEG molecules may be coupled to sulfhydryl groups on a binding polypeptide (Sartore et al., *Appl. Biochem. Biotechnol.*, 27, 45 (1991); Morpurgo et al., *Biocon. Chem.*, 7, 363-368 (1996); Goodson et al., *Bio/Technology* (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into a binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (see Himanen et al., *Nature.* (2001) 20-27; 414 (6866):933-8) and thus the surface-exposed residues identified. In one embodiment, cysteine residues are introduced into binding polypeptides at or near the N- and/or C-terminus, or within loop regions.

In some embodiments, the pegylated binding polypeptide comprises a PEG molecule covalently attached to the alpha amino group of the N-terminal amino acid. Site specific N-terminal reductive amination is described in Pepinsky et al., (2001) *JPET,* 297, 1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) *J. Biol. Chem.* 254,12579, and in Chamow et al., (1994) *Bioconjugate Chem.* 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Patent Publication 2002/0044921 and in WO094/014511.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., *Bioconjug. Chem.* 2004; 15(5):11005-1009.

Monopegylation of a binding polypeptide can also be produced according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of a binding polypeptide to activated PEG in the conjugation reaction can be from about 1:0.5 to 1:50, between from about 1:1 to 1:30, or from about 1:5 to 1:1.5.

Various aqueous buffers can be used in the present method to catalyze the covalent addition of PEG to the binding polypeptide. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated binding polypeptide, such as size exclusion (e.g. gel filtration) and ion exchange chromatography. Products may also be separated using SDS-PAGE. Products that may be separated include mono-, di-, tri-poly- and un-pegylated binding polypeptide, as well as free PEG. The percentage of mono-PEG conjugates can be controlled by pooling broader fractions around the elution peak to increase the percentage of mono-PEG in the composition. About ninety-percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, PEGylated binding polypeptide of the invention contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, optionally from about 10,000 Da to 36,000 Da. In a one embodiment, the PEG in pegylated binding polypeptide is a substantially linear, straight-chain PEG.

In one embodiment of the invention, the PEG in pegylated binding polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated binding polypeptides of the invention will preferably retain at least 25%, 50%, 60%, 70%, 80%, 85%, 90%, 95% or 100% of the biological activity associated with the unmodified protein. In one embodiment, biological activity refers to its ability to bind to CXCR3, as assessed by KD, $k_{on}$ or $k_{off}$. In one specific embodiment, the pegylated binding polypeptide protein shows an increase in binding to CXCR3 relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half-life, such as the half-life of the protein in the serum or other bodily fluid of an animal.

Therapeutic Formulations and Modes of Administration

The present disclosure features methods for treating conditions or preventing pre-conditions which respond to an inhibition of CXCR3 biological activity. Preferred examples are conditions that are characterized by inflammation or cellular hyperproliferation. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Exemplary Uses

The CXCR3 binding proteins described herein and their related variants are useful in a number of therapeutic and diagnostic applications. These include the inhibition of the biological activity of CXCR3 by competing for or blocking the binding to a CXCR3 as well as the delivery of cytotoxic or imaging moieties to cells, preferably cells expressing CXCR3. The small size and stable structure of these molecules can be particularly valuable with respect to manufacturing of the drug, rapid clearance from the body for certain applications where rapid clearance is desired or formulation into novel delivery systems that are suitable or improved using a molecule with such characteristics.

On the basis of their efficacy as inhibitors of CXCR3 biological activity, the polypeptides of this disclosure are effective against a number of cancer conditions as well as complications arising from cancer, such as pleural effusion and ascites, colorectal cancers, leukemias, lymphomas, head and neck cancers, small cell lung cancer, non-small cell lung cancer (NSCLC) and pancreatic cancer. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer.

A CXCR3 binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above. Preferably, in breast cancer the combination is with Herceptin or other Her-2 therapies.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-CXCR3 antibodies agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds has been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, Neomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, foliate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epipodophyllotoxins (etoposide, teniposide), DNA damaging agents (actinomycin, amsacrine, anthracyclines, Neomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prenisolone); growth factor signal transduction kinase inhibitors; mitochondrial dysfunction inducers and caspase activators; and chromatin disruptors.

Depending on the nature of the combinatory therapy, administration of the polypeptide therapeutic agents may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

In one example of a diagnostic application, a biological sample, such as serum or a tissue biopsy, from a patient suspected of having a condition characterized by inappropriate angiogenesis is contacted with a detectably labeled polypeptide of the disclosure to detect levels of CXCR3. The levels of CXCR3 detected are then compared to levels of CXCR3 detected in a normal sample also contacted with the labelled polypeptide. An increase of at least 10%, 20%, 30%, 40%, 50%, 60%, 70%, 80%, or 90% in the levels of the CXCR3 may be considered a diagnostic indicator.

In certain embodiments, the CXCR3 binding polypeptides are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}K$, $^{52}Fe$, $^{57}Co$, $^{67}Cu$, $^{67}Ga$, $^{68}Ga$, $^{123}I$, $^{125}I$, $^{131}I$, $^{132}I$, or $^{99}Tc$. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. Immunoscintigraphy using CXCR3 binding polypeptides directed at CXCR3 may be used to detect and/or diagnose cancers and vasculature. For example, any of the binding polypeptide against a CXCR3 marker labelled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The CXCR3 binding polypeptides can also be used to deliver additional therapeutic agents (including but not limited to drug compounds, chemotherapeutic compounds, and radiotherapeutic compounds) to a cell or tissue expressing CXCR3. In one example, the CXCR3 binding polypeptide is fused to a chemotherapeutic agent for targeted delivery of the chemotherapeutic agent to a tumor cell or tissue expressing CXCR3.

The CXCR3 binding polypeptides are useful in a variety of applications, including research, diagnostic and therapeutic applications. For instance, they can be used to isolate and/or purify receptor or portions thereof, and to study receptor structure (e.g., conformation) and function.

In certain aspects, the various binding polypeptides can be used to detect or measure the expression of CXCR3, for example, on endothelial cells (e.g., venous endothelial cells), or on cells transfected with a CXCR3 gene. Thus, they also have utility in applications such as cell sorting and imaging (e.g., flow cytometry, and fluorescence activated cell sorting), for diagnostic or research purposes.

In certain embodiments, the binding polypeptides of fragments thereof can be labeled or unlabeled for diagnostic purposes. Typically, diagnostic assays entail detecting the formation of a complex resulting from the binding of a binding polypeptide to CXCR3. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a CXCR3 protein is combined with the subject binding polypeptides, binding occurs between the binding polypeptides and the CXCR3 protein. In one embodiment, a sample containing cells expressing a CXCR3 protein (e.g., endothelial cells) is combined with the subject antibodies, and binding occurs between the binding polypeptides and cells bearing a CXCR3 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labelled polypeptide (e.g., an antibody) can be added which recognizes the subject binding polypeptide.

In certain aspects, kits for use in detecting the presence of a CXCR3 protein in a biological sample can also be prepared. Such kits will include a CXCR3 binding polypeptide which binds to a CXCR3 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present disclosure also provides a method of detecting and/or quantitating expression of CXCR3, wherein a composition comprising a cell or fraction thereof (e.g., membrane fraction is contacted with a binding polypeptide which binds to a CXCR3 or portion of the receptor under conditions appropriate for binding thereto, and the binding is monitored. Detection of the binding polypeptide, indicative of the formation of a complex between binding polypeptide and CXCR3 or a portion thereof, indicates the presence of the receptor. Binding of a polypeptide to the cell can be determined by standard methods, such as those described in the working examples. The method can be used to detect expression of CXCR3 on cells from an individual. Optionally, a quantitative expression of CXCR3 on the surface of endothelial cells can be evaluated, for instance, by flow cytometry, and the staining intensity can be correlated with disease susceptibility, progression or risk.

The present disclosure also provides a method of detecting the susceptibility of a mammal to certain diseases. To illustrate, the method can be used to detect the susceptibility of a mammal to diseases which progress based on the amount of CXCR3 present on cells and/or the number of CXCR3-positive cells in a mammal.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

The following terms, unless otherwise indicated, shall be understood to have the following meanings:

The terms "CXCR3 inhibitor" and "CXCR3 antagonist" are used interchangeably. Each is a molecule that detectably inhibits at least one function of CXCR3. Conversely, an "CXCR3 agonist" is a molecule that detectably increases at least one function of CXCR3. The inhibition caused by an CXCR3 inhibitor need not be complete so long as it is detectable using an assay. Any assay of a function of CXCR3 can be used, examples of which are provided herein. Examples of functions of CXCR3 that can be inhibited by a CXCR3 inhibitor, or increased by a CXCR3agonist, include cancer cell growth or apoptosis (programmed cell death), and so on. Examples of types of CXCR3 inhibitors and CXCR3 agonists include, but are not limited to, CXCR3 binding polypeptides such as antigen binding proteins (e.g., CXCR3 inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule in a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-CXCR3 antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CXCR3) if it binds to the antigen with a dissociation constant of 1 nanomolar or less.

An "antigen binding domain, "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to CXCR3, (preferably, human CXCR3). Antigen binding proteins include antigen binding proteins that inhibit a biological activity of CXCR3.

Oligomers that contain one or more antigen binding proteins may be employed as CXCR3 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have CXCR3 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a CXCR3 binding fragment of an anti-CXCR3 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Imminol.* 6:267-78. In one approach, recombinant fusion proteins comprising an anti-CXCR3 antibody fragment or derivative fused to a leucine zipper peptide are expressed in suitable host cells, and the soluble oligomeric anti-CXCR3 antibody fragments or derivatives that form are recovered from the culture supernatant.

Antigen-binding fragments of antigen binding proteins of the invention may be produced by conventional techniques. Examples of such fragments include, but are not limited to, Fab and F(ab')$_2$ fragments.

The present disclosure provides monoclonal antibodies that bind to CXCR3. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing have high fusion efficiency, and enzyme deficiencies that render them incapable of growing in certain selective media which support the growth of only the desired fused cells (hybridomas). Examples of suitable cell lines for use in mouse fusions include Sp-20, P3-X63/A28, P3-X63-Ag8.653, NS1/1.A4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against CXCR3 can be used, for example, in assays to detect the presence of CXCR3 polypeptides, either in vitro or in vivo. The antigen binding proteins also may be employed in purifying CXCR3 proteins by immunoaffinity chromatography. Blocking antigen binding proteins can be used in the methods disclosed herein. Such antigen binding proteins that function as CXCR3 antagonists may be employed in treating any CXCR3-induced condition, including but not limited to various cancers.

Antigen binding proteins may be employed in an in vitro procedure, or administered in vivo to inhibit CXCR3-induced biological activity. Disorders caused or exacerbated (directly or indirectly) by the proteolytic activation of CXCR3, examples of which are provided herein, thus may be treated. In one embodiment, the present invention provides a therapeutic method comprising in vivo administration of a CXCR3 blocking antigen binding protein to a mammal in need thereof in an amount effective for reducing a CXCR3-induced biological activity.

Antigen binding proteins include fully human monoclonal antibodies that inhibit a biological activity of CXCR3.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or *bacilli*. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of CXCR3 bound thereto. Polypeptides contemplated for use herein include substantially homogeneous recombinant mammalian anti-CXCR3 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-CXCR3 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for CXCR3 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from CXCR3. In one embodiment, the antigen binding protein has a $K_{off}$ of $1 \times 10^{-4}$ to $^{-1}$ or lower. In another embodiment, the $K_{off}$ is $5 \times 10^{-5}$ to $^{-1}$ or lower. In another embodiment, the $K_{off}$ is substantially the same as an antibody described herein. In another embodiment, the antigen binding protein binds to CXCR3 with substantially the same $K_{off}$ as an antibody described herein.

In another aspect, the present disclosure provides an antigen binding protein that inhibits an activity of CXCR3. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of CXCR3 with substantially the same $IC_{50}$ as an antibody described herein.

In another aspect, the present disclosure provides an antigen binding protein that binds to human CXCR3 expressed on the surface of a cell and, when so bound, inhibits CXCR3 signaling activity in the cell without causing a significant reduction in the amount of CXCR3 on the surface of the cell. Any method for determining or estimating the amount of CXCR3 on the surface and/or in the interior of the cell can be used. In other embodiments, binding of the antigen binding protein to the CXCR3-expressing cell causes less than about 75%, 50%, 40%, 30%, 20%, 15%, 10%, 5%, 1%, or 0.1 of the cell-surface CXCR3 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of CXCR3, or to an epitope of CXCR3 and an epitope of another molecule, via two different antigen binding sites or regions. Moreover, bispecific antigen binding protein as disclosed herein can comprise an CXCR3 binding site from one of the herein-described antibodies and a second CXCR3 binding region from another of the herein-described antibodies, including those described herein by reference to other publications. Alternatively, a bispecific antigen binding protein may comprise an antigen binding site from one of the herein described antibodies and a second antigen binding site from another CXCR3 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. No. 5,959, 083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGy-lated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurroli-done), polyethylene glycols, propropylene glycol homopolymers, polypropylene oxide/ethylene oxide co-polymers, polyoxyethylated polyols and polyvinyl alcohols.

95% Homology

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)), Near et al. Mol. Immunol. 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2).

Indications

In one aspect, the present disclosure provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). Among the conditions to be treated are conditions characterized by inappropriate expression or activity of CXCR3. In some such conditions, the expression or activity level is too high, and the treatment comprises administering a CXCR3 antagonist as described herein. The disorders or conditions are cancer-related. In particular, those cancers include, but are not limited to, breast, lung, ovarian and colon carcinoma and various myelomas.

Specific medical conditions and diseases that are treatable or preventable with the antigen binding proteins of this disclosure include various cancers.

Therapeutic Methods and Administration of Antigen Binding Proteins

Certain methods provided herein comprise administering a CXCR3 binding antigen binding protein to a subject, thereby reducing a CXCR3-induced biological response that plays a role in a particular condition. In particular embodiments, methods of the invention involve contacting endogenous CXCR3 with an CXCR3 binding antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient a CXCR3 antagonist in an amount and for a time sufficient to induce a sustained improvement over baseline of an indicator that reflects the severity of the particular disorder.

As is understood in the pertinent field, pharmaceutical compositions comprising the antibodies and fragments thereof of the disclosure are administered to a subject in a manner appropriate to the indication. Pharmaceutical compositions may be administered by any suitable technique, including but not limited to, parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments, Use of antigen binding proteins in ex vivo procedures also is contemplated. For example, a patient's blood or other bodily fluid may be contacted with an antigen binding protein that binds CXCR3 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to an CXCR3 binding antigen binding protein.

Combination Therapy

In another aspect, the present disclosure provides a method of treating a subject with an CXCR3 inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue.

In another embodiment, a combination therapy method comprises administering to the subject two, three, four, five, six, or more of the CXCR3 agonists or antagonists described herein. In another embodiment, the method comprises administering to the subject two or more treatments that together inhibit or activate (directly or indirectly) CXCR3-mediated signal transduction. Examples of such methods include using combinations of two or more CXCR3 inhibiting antigen binding proteins, of an CXCR3 inhibiting antigen binding protein and one or more other therapeutic moiety having anti-cancer properties (for example, cytotoxic agents, and/or immunomodulators), or of an CXCR3 inhibiting antigen binding protein and one or more other treatments (e.g., surgery, or radiation). Furthermore, one or more anti-CXCR3 antibodies or antibody derivatives can be used in combination with one or more molecules or other treatments, wherein the other molecule(s) and/or treatment(s) do not directly bind to or affect CXCR3, but which combination is effective for treating or preventing the condition being treated. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the CXCR3 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

Example 1

This example shows a cellular binding assay to determine the specific binding of anti-CXCR3 antibodies to CXCR3 expressed on a stable cell line. CHO-CXCR3 cells were lifted from culture flasks using non-enzymatic Cell Dissociation Buffer—PBS based (Life Technologies #13151-014). Cells were resuspended in FACS Buffer (2% Fetal Bovine Serum in PBS) at $1\times10^6$ cells/ml and 50 µl ($0.5\times10^5$ cells) were aliquoted into the wells of a 96-well plate. At the same time, CHO cells expressing an unrelated protein were treated in the same manner. Aliquots of antibody to give two different final concentrations, most often 5 and 10 were added to the cells and incubated for 1 hour at 4° C. and then washed twice with FACS Buffer. Cells were resuspended in 50 µl goat anti-human IgG (γ-chain specific)-PE conjugated secondary antibody (Southern Biotech #2040-09) diluted 1:500 in FACS Buffer. Cells were further incubated for 30 min at 4° C. and then washed 1× with FACS Buffer. The cells were resuspended in a final volume of 30 µl FACS Buffer and analyzed using the Flow Cytometer. Median fluorescence in the FL-2H channel was determined using FlowJo software. Binding of each antibody to the CHO-CXCR3 cell line was compared to binding to a control CHO cell line. The list of antibodies that showed specific binding to CHO-CXCR3 cells is shown in Table 1.

TABLE 1

Antibodies that bind to CHO-CXCR3.

| Name | Binding to hu-CXCR3 CHO |
| --- | --- |
| B2 | yes |
| C12 | yes |
| F7 | yes |
| 2A3 | yes |
| 3A3 | yes |
| 3A11 | yes |
| 3C11 | yes |
| 4D5 | yes |
| 32B12 | yes |
| 32D12 | yes |
| H1 | yes |
| C4 | yes |
| 3A7 | yes |
| 3A8 | yes |
| 3A5 | yes |

Example 2

This example shows a cellular binding assay to determine the $EC_{50}$ for anti-CXCR3 antibodies binding to human CXCR3. This example shows the binding characteristics for these antibodies in terms of the maximal cell binding and the concentration at which 50% binding saturation ($EC_{50}$) is reached. In this example, CHO-CXCR3 cells were lifted from culture flasks using non-enzymatic Cell Dissociation Buffer—PBS based (Life Technologies #13151-014). Cells were resuspended in FACS Buffer (2% Fetal Bovine Serum in PBS) at $1\times10^6$ cells/ml and 50 µl ($0.5\times10^5$ cells) were aliquoted into the wells of a 96-well plate. Plated cells were spun down and the supernatant discarded. Cells were resuspended in 30 µl FACS Buffer containing serially diluted concentrations of antibody in triplicate. Plates were incubated for 1 hr at 4° C. and then washed twice with FACS Buffer. Cells were resuspended in 50 µl goat anti-human IgG (γ-chain specific)-PE conjugated secondary antibody (Southern Biotech #2040-09) diluted 1:500 in FACS Buffer. Cells were further incubated for 30 min at 4° C. and then washed 1× with FACS Buffer. The cells were resuspended in a final volume of 30 µl FACS Buffer and analyzed using the Flow Cytometer. Median fluorescence in the FL-2H channel was determined using FlowJo software and $EC_{50}$ value was determined by plotting the data in GraphPad Prism and analyzing using a variable slope non-linear regression. The results are shown in Table 2.

TABLE 2

$EC_{50}$ of anti-CXCR3 antibodies to human CXCR3.

| Name | EC50 (nM), hu-CXCR3 CHO |
|---|---|
| B2 | 0.7 |
| C12 | 15 |
| F7 | 5 |
| 2A3 | 11 |
| 3A3 | 0.5 |
| 3A11 | 1.2 |
| 3C11 | 0.6 |
| 4D5 | 7 |
| 32B12 | 1 |
| 32D12 | 4 |

Example 3

This example shows a cellular binding assay to determine the $EC_{50}$ for anti-CXCR3 antibodies binding to murine CXCR3. This example shows the binding characteristics for these antibodies in terms of the maximal cell binding and the concentration at which 50% binding saturation ($EC_{50}$) is reached. In this example, murine B16-F10 cells (ATCC, #CRL-6475) were lifted from culture flasks using non-enzymatic Cell Dissociation Buffer—PBS based (Life Technologies #13151-014). Cells were harvested, washed and resuspended in FACS Buffer (2% Fetal Bovine Serum in PBS) at $1\times10^6$ cells/ml and 50 µl ($0.5\times10^5$ cells) were aliquoted into the wells of a 96-well plate. Plated cells were spun down and the supernatant discarded. Cells were resuspended in 30 µl FACS Buffer serially diluted concentrations of antibody in triplicate. Plates were incubated for 1 hr at 4° C. and then washed 2× with FACS Buffer. Cells were resuspended in 50 µl goat anti-human IgG (γ-chain specific)-PE conjugated secondary antibody (Southern Biotech #2040-09) diluted 1:500 in FACS Buffer. Cells were further incubated for 30 min at 4° C. and then washed 1× with FACS Buffer. The cells were resuspended in a final volume of 30 µl FACS Buffer and analyzed using the Flow Cytometer. Median fluorescence in the FL-2H channel was determined using FlowJo software and the $EC_{50}$ value was determined by plotting the data in GraphPad Prism and analyzing using a variable slope non-linear regression. The results are shown in Table 3.

TABLE 3

$EC_{50}$ of anti-CXCR3 antibodies to murine CXCR3.

| Name | EC50 (nM), mur CXCR3 |
|---|---|
| 32B12 | 25 |

Example 4

In this example, CHO-CXCR3 cells were lifted from culture flasks using non-enzymatic Cell Dissociation Buffer—PBS based (Life Technologies #13151-014). Cells were resuspended in FACS Buffer (2% Fetal Bovine Serum in PBS) with sodium azide at $1\times10^6$ cells/ml and 800 µl were aliquoted into a tube for each antibody. Antibody was added to a final concentration of 5 µg/ml and incubated at room temperature for 1 h. The samples were placed on ice and a 105 µl aliquot at various time points was added to 190 µl FACS buffer in a 96-well plate and centrifuged for 3 min. Supernatant was discarded, the cells were resuspended in 105 µl of FACS buffer, duplicate aliquots (50 µl) added to another 96-well plate containing 150 µl FACS buffer and incubated at room temperature. After all of the time points were collected, the plate was centrifuged for 3 min, supernatant discarded and the cells resuspended in 50 µl goat anti-human IgG (γ-chain specific)-PE conjugated secondary antibody (Southern Biotech #2040-09) diluted 1:500 in FACS Buffer. Cells were incubated for 30 min at 4° C. and then washed 1× with FACS Buffer. The cells were resuspended in a final volume of 30 µl FACS Buffer and analyzed using the Flow Cytometer. The binding of clone 32B12 over time is shown in FIG. 1.

Example 5

This example shows a calcium assay using anti-CXCR3 antibodies. CHO-CXCR3 cells (CHO cells transfected with human CXCR3 gene) were used in calcium assay. Aliquots of $0.1\times10^5$ cells were seeded in 20 µl of growth medium per well of a 384 well plate (#781091, Greiner) and incubated for 20 hours. The growth medium was F-12K (#21127, Life Technologies) plus 10% FBS. 5 µl of serial diluted antibodies were added into 20 µl cells and incubated 20 min at room temperature. Then 25 µl of Calcium 4 Assay kit (R8142, Molecular Devices) including 0.5 mM probenecid (Sigma #P8761-25G) were added to the 25 µl cells pre-incubated with the antibodies. After 1 h incubation at 37° C. 5% $CO_2$ followed by 15 minutes at room temperature, 12.5 µl of 5× dose of ligands were added to each well of the plate as the challenge agonist during detection on the FlexStation3. The final concentration of each ligand used in the assay was 200 nM of CXCL9 (#300-26, PeproTech), 164 nM of CXCL10 (#300-12, PeproTech) and 60 nM of CXCL11 (#300-46, PeproTech). The $IC_{50}$ value of each antibody shown in the table was calculated using Prism5. The $IC_{50}$ of each antibody with each corresponding ligand is shown in Table 4. Each $IC_{50}$ value represents the Mean (n=2). The control antibody is from R&D (Cat#MAB160, R&D).

TABLE 4

IC$_{50}$ [nM] of anti-CXCR3 antibodies in a
calcium flux assay using CHO-CXCR3 cells

|  | CXCL9 | CXCL10 | CXCL11 |
|---|---|---|---|
| R&D mAb | n.d. | n.d. | 23 |
| 32B12 | 37 | 7 | 16 |
| 32D12 | n.d. | n.d. | 19 |

Note:
n.d. = not determined

Example 6

This example describes chemotaxis assays using activated human T cells. Primary human T cells activated by anti-CD3 (1 ng/ml) for 2 days were used for prepared. Chemotaxis assays were set up using a 96-well chemotaxis chamber (ChemoTX: NeuroProbe, Gaithersburg, Md.) with the 2 compartments separated by a 5-μm polycarbonate membrane. The assay buffer used for chemotaxis was RPMI plus 0.5% BSA. Serially-diluted concentrations of antibodies were pre-incubated with the activated T cells (0.1×10$^6$ cells in 25 μl of the assay buffer) at room temperature for 20 min. The ligands CXCL9 (30 nM), CXCL10 (12.5 nM) and CXCL11 (0.3 nM) were loaded respectively in the wells of plate in the lower chambers, whereas the cells pre-incubated with antibodies were loaded on top of membrane. After 2 h incubation at 37° C., 5% CO$_2$, migrated cells in the lower chamber were transferred to an opaque white 96-well plate and incubated with CellTiter GLo (Cat #G7571, Promega) for 10 min at room temperature. Luminescent signals generated from the cells in each well were detected by a fluorescent plate reader (HexStation3, Molecular Device). The IC$_{50}$ value of each mAb indicated in the table was calculated by Prism5. The IC$_{50}$ of the each mAb against corresponding ligands is indicated in Table 5. Each IC$_{50}$ value represents Mean (n=2). The control antibody was from R&D (Cat#MAB160, R&D).

TABLE 5

IC$_{50}$ [nM] of anti-CXCR3 antibodies in a
chemotaxis assay using activated T cells

|  | CXCL9 | CXCL10 | CXCL11 |
|---|---|---|---|
| R&D mAb | 1 | 1.8 | 0.4 |
| 32B12 | 0.6 | 0.2 | 0.3 |
| 32D12 | 2.5 | 0.03 | 3.4 |

Sequence Listing

| | Heavy chain variable domain region | Light chain variable domain region |
|---|---|---|
| 32B12 | EVQLVQSGGGLVKSGRSLRLSCTVSGFTFGNSAMS WFRQAPGKGLEWVSSISSSSSYIYYADSVKGRFTISR DNAKNSLYLQMNSLRAEDTAVYYCARDLSGRGYSY LNYWGQGTLVTVSS SEQ ID NO. 1 | SYELTQPPSVSAAPGQKVTISCSGSSSNIGNS YVSWFQQFPGTAPKLVIYENNKRPSGIPDRF SGSKSGTSATLGITGLQTGDEADYYCGTWD SSLSGRVFGGGTKLTVL SEQ ID NO. 2 |
| 32D12 | EVQLLESGGGLVQPGGSQRLSCAASGFTFSSYPMT WVRQAPGKGLEWVSAISDGGSGTYYADSVKGRFTI SRDNSKNTLYLQMNSLRAEDTAIYYCARYKMGGSY RGLDDWGQGTLVTVSS SEQ ID NO. 3 | LPVLTQPASVSGSPGQPITISCTGTSGNIGSY NYVSWYQQHPGKAPRLLIYDVSLRPSGISSH FSGSKSGNTASLTISGLQAEDEAEYFCLSWT SDKTYVFGSGTKLTVL SEQ ID NO. 4 |
| H1 | EVQLLESGGGVVQPGRSLRLSCAASGFTFRYYGMH WVRQAPGKGLEWVAAIRNDGSNEYYADSVKGRFTI SRDNSKNTLYLEMNSLRAEDTSVYHCARDGFYRGSP YYFDSWGQGTLVTVSS SEQ ID NO. 5 | QAGLTQPPSVSAAPGQKVTISCSGSSSNIGN NYVSWYQQLPGTAPKLLIYDNKRRPSGMP DRFSGSKSGTSATLGITGLQTGDEADYYCGT WDSSLSAVVFGGGTKLTVL SEQ ID NO. 6 |
| B7 | QVQLVQSGAEVKKPGSSVKVSCKASGGTFKRYSVH WVRQAPGQGLEWVGRIVPFLGLANYAQKFQGRVT ITADTSTNTTYMDLRSLRSEDTAVYYCVRSTGYLDY WGQGTLVTVSS SEQ ID NO. 7 | DIVMTQTPLSSPVTLGQPASISCRSSQSLVH SDGNTYLSWFQQRPGQSPRRLIYKVSNRDS GVPDRFSGSGSGTDFTLKISRVEAEDVGVYF CLQSLQLPITFGQGTKVEIK SEQ ID NO. 8 |
| C12 | QVQLVQSGAEVKKPGSSMKVSCKTSGGTFNAYAIT WVRQAPGQGLEWMGRIVPVLGMVSYVQKFQGRL TITADKSTSTTYMELSSLTSDDTAVYYCARQTGDSDH WGPGTLVTVSS SEQ ID NO. 9 | DIVMTQSPLSLPVTLGQPASISCRSSQSLVYS DGNTYLNWFQQRPGQSPRRLIYKVSNRESG VPDRFSGSGSGTDFTLKISRVEAEDVGVYYC MQGTHWPNTFGGXTKLEIK SEQ ID NO. 10 |
| D12 | QMQLVQSGAEVKKPGASVKVSCKASGYTFTSYYM HWVRQAPGQGLEWMGIINPSAGSTSYAQKFQGR VTMTRDTSTSTVYMELSSLGSEDTAVYYCASRSFGN DGVFDIWGQGTMVTVSS SEQ ID NO. 11 | QTVVTQPPSVSGAPGQRVTVSCTGSSSNIG SRYAVNWYQQLPGRAPKLLIYGNTNRPSGV PDRFSASKSGTSASLAISGLQAEDEADYYCQ SFDSSLRGYVFGTGTKVTVL SEQ ID NO. 12 S |
| E1 | EVQLVESGGGVVQPGRSLRLSCAASEFTESSYTIHW VRQAPGKGLEWVGRIHPKSEGGTTDYAAPVKGRFLI SRDDSENTMYLQMNSLQTEDTAVYYCATYGSGSH WIWGQGTLVTVSS SEQ ID NO. 13 | DVVMTQTPSTLSASVGDRVTITCRASQSIKT WLAWYQQRPGKAPKRLIYAASSLQSGVPSR FSGSGSGTEFTLTISSLQPEDFATYYCVQHNS YPITFGQGTRLEIK SEQ ID NO. 14 |
| G12 | EVQLVESGGGVVQPGKSLRLSCAASGFTFSSYGMH WVRQAPGKGLEWVAVISYDGSNKYYADSVKGRFTI SRDNSKNTLYLQMNSLRAEDTAVYYCAYGGFSHW GQGTLVTVSS SEQ ID NO. 15 | DIVMTQTPLSLPVTLGQPASLSCRSSQSLAH RDGNTYLSWFQQRPGQSPRRLIYKVSNRDS GVPDRFSGSGSGTDFTLKISRVEAEDVGVYY CMQGTHWPPTFGGGTKVEIK SEQ ID NO. 16 |

| | Heavy chain variable domain region | Light chain variable domain region |
|---|---|---|
| 3A3 | QVQLVQSGAEVKKPGSSVKVSCKASGGTFNRYAFS WVRQAPGQGPELMGRIMPMFDIASYAQKFQGRLT ITADKSTSTAYMELSSLRSDDTAVYYCTQVSGDSDY WGPGTLVTVSS SEQ ID NO. 17 | DIVMTQTPLSLPVTLGQPASISCRSSQSLVH NDGNTYLNWFHQRPGQSPRRLIYKVSNRD FGVPDRFSGSGSGTDFTLRISRVEAEDVGVY YCMQGSHWPLTFGGGTKVEIK SEQ ID NO. 18 |
| 3A5 | QVQLVQSGAEVKKPGSSVKVACKASGGTFSHSAIS WVRQAPGQGLEWIGRTIPTLEMASYAQKFQGRVTI SADKSTRTGYMELRDLRSEDTAVYYCSTQTPSYTDH WGQGTLVTVSS SEQ ID NO 19 | DVVMTQTPLSLPVTLGQPASISCRSSQSLVY RDGNTYLNWFQQRPGQSPRRLIYKVSNRDS SGVPDRFSGSGSGTDFTLKISRVEAEDVGVY YCMQGTHWPITFGQGTKVEIK SEQ ID NO. 20 |
| 3A11 | QVQLVQSGGGLVKPGGSLRLSCAASGFTFTSSGMN WVRQAPGKGLEWVAYIFPNGKTLYPESVKGRFIITR DNAEKSLFLEMNNLRAEDMGVYYCAIDLNWGSGY WGQGTLVTVSS SEQ ID NO 21 | SYVLTQPPSVSKGLRQTATLTCTGNINNVG NVGATWLQQHQGHPPKLLSDRNNNRPSGI SERFSASRSGNAASLTITGLQPEDEADYYCS AWDTSLGAWVFGGGTKLTVL SEQ ID NO. 22 |
| 3B12 | EVQLVESGGGVVQPGRSLRLSCAASGFTFSHYGMH WVRQAPGKGLEWVAVISYDGSKKSYADSVKGRFTI SRDNSKNTLYLQMNSLRADDTAVYYCATSAGGGGY WGQGTLVTVSS SEQ ID NO 23 | QSVLTQPPSVSKDLRQTATLTCTGNSNNVG DKGAAWLQQHQGHPPKLLSYRNNNRPSGI SERLSASRSGNTASLTITGLQPDDEADYYCS AWDSSLSAWVFGGGTKLTVL SEQ ID NO. 24 |
| 3C11 | EVQLVESGGGLVQPGGSLRLSCSASGFTFSSYAMH WVRQAPGKGLEYVSAISSNGGSTYYADSVKGRFTIS RDNSKNTLYLQMSSLRAEDTAVYYCVKSIAAAGTQY YYYYMDVWGKGTTVTVSS SEQ ID NO 25 | DIQLTQSPSSLSASVGDRVTITCRASQGIGTY LAWFQQKPGKVPKPLIYAASTLQSGVPSRFS GSGSGADFTLTISSLQPEDVATYYCQKYNSV PQTFGQGTKVEIK SEQ ID NO. 26 |
| 4C3 | QVQLVESGGGLVQPGRSLRLSCIISGFTFGDYTMSW FRQAPGKGLEWVGFIRSKAYGGTTQYAASVKGRFTI SRDDSKSIAYLQMNSLKTEDTAVYYCTRGDYGDFP WYFDLWGRGTLVTVSS SEQ ID NO 27 | AIQLTQSPLALPVPLGQPASISCRASQSLVYS NGNTYLNWFQLRPGQSPRRLIYKVSRRDSG VPDRFSGSGSDTDFTLKISRVEAEDVGVYYC MQATQWPITFGQGTRLEIK SEQ ID NO. 28 |
| B12 | QMQLVQSGAEVKKPGSSVKVSCKASGGTFNRYAFS WVRQAPGQGPELMGRIMPMFDIASYAQKFQGRLT ITADKSTSTAYMELSSLRSDDTAVYYCTQVSGDSDY WGPGTTVTVSS SEQ ID NO. 29 | DVVMTQSPLSLPVTLGQPASISCRSTESLVH SDGNTYLNWFHQRPGQSPRRLIYKISNRDS GVPDRFSGSGSGTDFTLKISRVEAEDVGVYY CFQGTHWPPTFGQGTKVEIK SEQ ID NO. 30 |
| C4 | QVQLVQSGAEVKKPGSSVKVACKASGGTFSHSAIS WVRQAPGQGLEWIGRTIPTLEMASYAQKFQGRVTI SADKSTRTGYMELRDLRSEDTAVYYCSTQTPSYTDH WGQGTLVTVSS SEQ ID NO. 31 | EIVLTQSPLSLPVTLGQPASISCNSSQSLLHR DGHTYLHWFQQRPGQSPRRLIYKVSNRDS GVPDKFSGSGSGTEFTLKISRVEAEDVGVYY CMQGTHWPLAFGGGTKLEIK SEQ ID NO. 32 |
| F7 | QVQLVQSGAEVKKPGSSVKVACKASGGTSHSAIS WVRQAPGQGLEWIGRTIPTLEMASYAQKFQGRVTI SADKSTRTGYMELRDLRSEDTAVYYCSTQTPSYTDH WGQGTLVTVSS SEQ ID NO. 31 | DIVMTQTPLSLPVTLGQPASISCRSNQSLVH SDGNTYLYWFQQRPGQSPRRLIYKVSNRDS GVPDRFSGSGSGTDFTLKINRVEAEDVGVYY CMQGTHWPNTGQGTKLEIK SEQ ID NO. 33 |
| 2A3 | QVQLVQSGAEVKKPGSSVKVACKASGGTFSHSAIS WVRQAPGQGLEWIGRTIPTLEMASYAQKFQGRVTI SADKSTRTGYMELRDLRSEDTAVYYCSTQTPSYTDH WGQGTLVTVSS SEQ ID NO. 31 | DIVMTQTPLSLPVTLGQPASISCRSSQSLVHS DGNTYLNWFQQRPGQSPRRLIYKVSNRDS GVPDRFSGSGSGTDFTLKISRVEAEDVGVYY CMQGTHWPLTFGGGTKVEIK SEQ ID NO. 34 |
| 3A7 | QVQLVQSGAEVKKPGSSVKVACKASGGTFSHSAIS WVRQAPGQGLEWIGRTIPTLEMASYAQKFQGRVTI SADKSTRTGYMELRDLRSEDTAVYYCSTQTPSYTDH WGQGTLVTVSS SEQ ID NO. 31 | DVVMTQSPVSLPVTLGQPASISCRSSQSLVH SDGNTYFNWFQQRPGQSPRRLIYKVSNRDS GVPDRFSGSGSGTDFTLKISRVEAEDVGVYY CMQGTHWPITFGQGTRLEIK SEQ ID NO. 35 |
| 3A8 | QVQLVQSGAEVKKPGSSVKVACKASGGTFSHSAIS WVRQAPGQGLEWIGRTIPTLEMASYAQKFQGRVTI SADKSTRTGYMELRDLRSEDTAVYYCSTQTPSYTDH WGQGTLVTVSS SEQ ID NO. 31 | DIVMTQTPLSLPVTLGQPAAISCRSSQSLVYS DGNTYLNWFHQRPGQSPRRLIYKVSNRDS GVPDRFSGSGSGTDFTLKISRVEAEDVGVYY CMQGTHWPLTFGGGTKLEIK SEQ ID NO. 36 |
| 4D5 | QVQLVQSGAEVKKPGSSVKVACKASGGTFSHSAIS WVRQAPGQGLEWIGRTIPTLEMASYAQKFQGRVTI SADKSTRGYMELRDLRSEDTAVYYCSTQTPSYTDH | DIVMTQSPLSLPVTLGQPASISCRSSHTLVHS DGTTYLNWFQQRPGQSPRRLIYKVSNRDSG VPDRFSGSGSGTDFTLKISRVEAEDVGVYYC |

| Sequence Listing | |
|---|---|
| Heavy chain variable domain region | Light chain variable domain region |
| WGQGTLVTVSS SEQ ID NO. 31 | MQGTHWPLTFGGGTKVEIK SEQ ID NO. 37 |

We claim:

1. A recombinant fully human anti-C-X-C chemokine receptor-3 (CXCR3) antibody, or an antigen-binding fragment thereof, comprising a heavy chain variable domain and a light chain variable domain, comprising complementarity determining regions (CDRs) as set forth in a heavy chain variable domain amino acid sequence comprising SEQ ID NO: 1 and a light chain variable domain amino acid sequence comprising SEQ ID NO: 2.

2. The recombinant fully human anti-CXCR3 antibody, or antigen binding fragment thereof, of claim 1, wherein the heavy chain variable domain and the light chain variable domain are at least 95% identical to the sequences of SEQ ID NO: 1 and SEQ ID NO: 2, respectively.

3. The recombinant fully human anti-CXCR3 antibody of claim 1, wherein the antibody is an IgG.

4. The recombinant fully human anti-CXCR3 antibody of claim 3, wherein the antibody is an IgG1 or an IgG4.

5. The recombinant fully human anti-CXCR3 antibody of claim 2, comprising a heavy chain variable domain comprising the heavy chain variable region amino acid sequence of SEQ ID NO: 1; and comprising a light chain variable domain comprising the light chain variable region amino acid sequence of SEQ ID NO: 2.

6. The recombinant fully human antigen binding fragment of claim 1, wherein the fragment is a Fab fragment or a single chain antibody.

7. The recombinant fully human antigen binding fragment of claim 2, wherein the fragment is a Fab fragment or a single chain antibody.

8. A pharmaceutical composition comprising the recombinant fully human anti-CXCR3 antibody, or antigen-binding fragment thereof, of claim 1, and a pharmaceutically acceptable excipient.

9. A method for inhibiting CXCR3 activity or delivering a cytotoxic agent to a CXCR3-expressing cell, comprising administering an effective amount of the recombinant fully human anti-CXCR3 antibody, or antigen-binding fragment thereof, of claim 1, to a subject in need thereof.

10. The method of claim 9, wherein the subject has a CXCR3-positive cancer selected from the group consisting of carcinoma, leukemia, lymphoma, prostate cancer, non-small cell lung cancer, breast cancer, endometrial cancer, ovarian cancer, gastric cancer, head and neck cancer, melanoma, osteosarcoma, intestinal and colon cancer, and metastatic cancer.

11. The method of claim 9, wherein the recombinant fully human anti-CXCR3 antibody, or antigen-binding fragment thereof, is classified as an isotype selected from the group consisting of: IgG, IgM, IgD, IgA, and IgE.

12. The method of claim 11, wherein the antibody is an IgG1 or an IgG4.

13. The method of claim 9, wherein the recombinant fully human antigen binding fragment is a Fab fragment or a single chain antibody.

14. The method of claim 9, wherein the recombinant fully human anti-CXCR3 antibody, or an antigen-binding fragment thereof, comprises the heavy chain variable domain comprising the amino acid sequence as set forth in SEQ ID NO: 1; and comprises the light chain variable domain comprising the amino acid sequence as set forth in SEQ ID NO: 2.

* * * * *

SEQUENCE LISTING

<160> NUMBER OF SEQ ID NOS: 42

<210> SEQ ID NO 1
<211> LENGTH: 121
<212> TYPE: PRT
<213> ORGANISM: Homo Sapiens

<400> SEQUENCE: 1

Glu Val Gln Leu Val Gln Ser Gly Gly Gly Leu Val Lys Ser Gly Arg
1               5                   10                  15

Ser Leu Arg Leu Ser Cys Thr Val Ser Gly Phe Thr Phe Gly Asn Ser
            20                  25                  30

Ala Met Ser Trp Phe Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Gly Arg Gly Tyr Ser Tyr Leu Asn Tyr Trp Gly
            100                 105                 110

Gln Gly Thr Leu Val Thr Val Ser Ser
        115                 120

<210> SEQ ID NO 2
<211> LENGTH: 110
<212> TYPE: PRT
<213> ORGANISM: Homo Sapiens

<400> SEQUENCE: 2

Ser Tyr Glu Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Ser
            20                  25                  30

Tyr Val Ser Trp Phe Gln Gln Phe Pro Gly Thr Ala Pro Lys Leu Val
        35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Arg Val Phe Gly Gly Gly Thr Lys Leu Thr Val Leu
            100                 105                 110

<210> SEQ ID NO 3
<211> LENGTH: 121
<212> TYPE: PRT

<213> ORGANISM: Homo Sapiens

<400> SEQUENCE: 3

```
Glu Val Gln Leu Leu Glu Ser Gly Gly Gly Leu Val Gln Pro Gly Gly
1               5                   10                  15

Ser Gln Arg Leu Ser Cys Ala Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ser Ala Ile Ser Asp Gly Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Tyr Lys Met Gly Gly Ser Tyr Arg Gly Leu Asp Asp Trp Gly
            100                 105                 110

Gln Gly Thr Leu Val Thr Val Ser Ser
            115                 120
```

<210> SEQ ID NO 4
<211> LENGTH: 110
<212> TYPE: PRT
<213> ORGANISM: Homo Sapiens

<400> SEQUENCE: 4

```
Leu Pro Val Leu Thr Gln Pro Ala Ser Val Ser Gly Ser Pro Gly Gln
1               5                   10                  15

Pro Ile Thr Ile Ser Cys Thr Gly Thr Ser Gly Asn Ile Gly Ser Tyr
            20                  25                  30

Asn Tyr Val Ser Trp Tyr Gln Gln His Pro Gly Lys Ala Pro Arg Leu
        35                  40                  45

Leu Ile Tyr Asp Val Ser Leu Arg Pro Ser Gly Ile Ser Ser His Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Glu Tyr Phe Cys Leu Ser Trp Thr Ser Asp
                85                  90                  95

Lys Thr Tyr Val Phe Gly Ser Gly Thr Lys Leu Thr Val Leu
            100                 105                 110
```

<210> SEQ ID NO 5
<211> LENGTH: 122
<212> TYPE: PRT
<213> ORGANISM: Homo Sapiens

<400> SEQUENCE: 5

```
Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Arg Tyr Tyr
            20                  25                  30

Gly Met His Trp Val Arg Gln Ala Pro Gly Lys Gly Leu Glu Trp Val
        35                  40                  45

Ala Ala Ile Arg Asn Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Glu Met Asn Ser Leu Arg Ala Glu Asp Thr Ser Val Tyr His Cys
                85                  90                  95

Ala Arg Asp Gly Phe Tyr Arg Gly Ser Pro Tyr Tyr Phe Asp Ser Trp
            100                 105                 110

Gly Gln Gly Thr Leu Val Thr Val Ser Ser
        115                 120
```

<210> SEQ ID NO 6
<211> LENGTH: 110
<212> TYPE: PRT
<213> ORGANISM: Homo Sapiens

<400> SEQUENCE: 6

```
Gln Ala Gly Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Leu Pro Gly Thr Ala Pro Lys Leu Leu
            35                  40                  45

Ile Tyr Asp Asn Lys Arg Arg Pro Ser Gly Met Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Thr Lys Leu Thr Val Leu
            100                 105                 110
```

<210> SEQ ID NO 7
<211> LENGTH: 116
<212> TYPE: PRT
<213> ORGANISM: Homo Sapiens

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Lys Arg Tyr
            20                  25                  30

Ser Val His Trp Val Arg Gln Ala Pro Gly Gln Gly Leu Glu Trp Val
            35                  40                  45

Gly Arg Ile Val Pro Phe Leu Gly Leu Ala Asn Tyr Ala Gln Lys Phe
50                  55                  60

Gln Gly Arg Val Thr Ile Thr Ala Asp Thr Ser Thr Asn Thr Thr Tyr
65                  70                  75                  80

Met Asp Leu Arg Ser Leu Arg Ser Glu Asp Thr Ala Val Tyr Tyr Cys
                85                  90                  95

Val Arg Ser Thr Gly Tyr Leu Asp Tyr Trp Gly Gln Gly Thr Leu Val
            100                 105                 110

Thr Val Ser Ser
        115
```

<210> SEQ ID NO 8
<211> LENGTH: 112
<212> TYPE: PRT
<213> ORGANISM: Homo Sapiens

<400> SEQUENCE: 8

-continued

Asp Ile Val Met Thr Gln Thr Pro Leu Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Ser
                85                  90                  95

Leu Gln Leu Pro Ile Thr Phe Gly Gln Gly Thr Lys Val Glu Ile Lys
            100                 105                 110

<210> SEQ ID NO 9
<211> LENGTH: 116
<212> TYPE: PRT
<213> ORGANISM: Homo Sapiens

<400> SEQUENCE: 9

Gln Val Gln Leu Val Gln Ser Gly Ala Glu Val Lys Lys Pro Gly Ser
1               5                   10                  15

Ser Met Lys Val Ser Cys Lys Val Ser Gly Gly Thr Phe Asn Ala Tyr
            20                  25                  30

Ala Ile Thr Trp Val Arg Gln Ala Pro Gly Gln Gly Leu Glu Trp Met
        35                  40                  45

Gly Arg Ile Val Pro Val Leu Gly Met Val Ser Tyr Val Gln Lys Phe
    50                  55                  60

Gln Gly Arg Leu Thr Ile Thr Ala Asp Lys Ser Thr Ser Thr Thr Tyr
65                  70                  75                  80

Met Glu Leu Ser Ser Leu Thr Ser Asp Asp Thr Ala Val Tyr Tyr Cys
                85                  90                  95

Ala Arg Gln Thr Gly Asp Ser Asp His Trp Gly Pro Gly Thr Leu Val
            100                 105                 110

Thr Val Ser Ser
115

<210> SEQ ID NO 10
<211> LENGTH: 112
<212> TYPE: PRT
<213> ORGANISM: Homo Sapiens
<220> FEATURE:
<221> NAME/KEY: misc_feature
<222> LOCATION: (106)..(106)
<223> OTHER INFORMATION: Xaa can be any naturally occurring amino acid

<400> SEQUENCE: 10

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Glu Ser Gly Val Pro
    50                  55                  60

Asp Arg Phe Ser Gly Ser Gly Ser Gly Thr Asp Phe Thr Leu Lys Ile
65                  70                  75                  80

-continued

Ser Arg Val Glu Ala Glu Asp Val Gly Val Tyr Tyr Cys Met Gln Gly
                85                  90                  95

Thr His Trp Pro Asn Thr Phe Gly Gly Xaa Thr Lys Leu Glu Ile Lys
            100                 105                 110

<210> SEQ ID NO 11
<211> LENGTH: 120
<212> TYPE: PRT
<213> ORGANISM: Homo Sapiens

<400> SEQUENCE: 11

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Ala Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Gly Ser Glu Asp Thr Ala Val Tyr Tyr Cys
                85                  90                  95

Ala Ser Arg Ser Phe Gly Asn Asp Gly Val Phe Asp Ile Trp Gly Gln
            100                 105                 110

Gly Thr Met Val Thr Val Ser Ser
        115                 120

<210> SEQ ID NO 12
<211> LENGTH: 111
<212> TYPE: PRT
<213> ORGANISM: Homo Sapiens

<400> SEQUENCE: 12

Gln Thr Val Val Thr Gln Pro Pro Ser Val Ser Gly Ala Pro Gly Gln
1               5                   10                  15

Arg Val Thr Val Ser Cys Thr Gly Ser Ser Ser Asn Ile Gly Ser Arg
            20                  25                  30

Tyr Ala Val Asn Trp Tyr Gln Gln Leu Pro Gly Arg Ala Pro Lys Leu
        35                  40                  45

Leu Ile Tyr Gly Asn Thr Asn Arg Pro Ser Gly Val Pro Asp Arg Phe
    50                  55                  60

Ser Ala Ser Lys Ser Gly Thr Ser Ala Ser Leu Ala Ile Ser Gly Leu
65                  70                  75                  80

Gln Ala Glu Asp Glu Ala Asp Tyr Tyr Cys Gln Ser Phe Asp Ser Ser
                85                  90                  95

Leu Arg Gly Tyr Val Phe Gly Thr Gly Thr Lys Val Thr Val Leu
            100                 105                 110

<210> SEQ ID NO 13
<211> LENGTH: 119
<212> TYPE: PRT
<213> ORGANISM: Homo Sapiens

<400> SEQUENCE: 13

Glu Val Gln Leu Val Glu Ser Gly Gly Gly Val Val Gln Pro Gly Arg
1               5                   10                  15

Ser Leu Arg Leu Ser Cys Ala Ala Ser Glu Phe Thr Phe Ser Ser Tyr
            20                  25                  30

Thr Ile His Trp Val Arg Gln Ala Pro Gly Lys Gly Leu Glu Trp Val
        35                  40                  45

Gly Arg Ile His Pro Lys Ser Glu Gly Gly Thr Thr Asp Tyr Ala Ala
 50                  55                  60

Pro Val Lys Gly Arg Phe Leu Ile Ser Arg Asp Asp Ser Glu Asn Thr
65                  70                  75                  80

Met Tyr Leu Gln Met Asn Ser Leu Gln Thr Glu Asp Thr Ala Val Tyr
                85                  90                  95

Tyr Cys Ala Thr Tyr Gly Ser Gly Ser His Trp Ile Trp Gly Gln Gly
            100                 105                 110

Thr Leu Val Thr Val Ser Ser
        115

<210> SEQ ID NO 14
<211> LENGTH: 107
<212> TYPE: PRT
<213> ORGANISM: Homo Sapiens

<400> SEQUENCE: 14

Asp Val Val Met Thr Gln Thr Pro Ser Thr Leu Ser Ala Ser Val Gly
1               5                   10                  15

Asp Arg Val Thr Ile Thr Cys Arg Ala Ser Gln Ser Ile Lys Thr Trp
            20                  25                  30

Leu Ala Trp Tyr Gln Gln Arg Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln His Asn Ser Tyr Pro Ile
                85                  90                  95

Thr Phe Gly Gln Gly Thr Arg Leu Glu Ile Lys
            100                 105

<210> SEQ ID NO 15
<211> LENGTH: 114
<212> TYPE: PRT
<213> ORGANISM: Homo Sapiens

<400> SEQUENCE: 15

Glu Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Gly Gly Phe Ser His Trp Gly Gln Gly Thr Leu Val Thr Val
            100                 105                 110

Ser Ser

<210> SEQ ID NO 16
<211> LENGTH: 112
<212> TYPE: PRT
<213> ORGANISM: Homo Sapiens

<400> SEQUENCE: 16

```
Asp Ile Val Met Thr Gln Thr Pro Leu Ser Leu Pro Val Thr Leu Gly
1               5                   10                  15

Gln Pro Ala Ser Leu Ser Cys Arg Ser Ser Gln Ser Leu Ala His Arg
            20                  25                  30

Asp Gly Asn Thr Tyr Leu Ser Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gly Gly Thr Lys Val Glu Ile Lys
            100                 105                 110
```

<210> SEQ ID NO 17
<211> LENGTH: 116
<212> TYPE: PRT
<213> ORGANISM: Homo Sapiens

<400> SEQUENCE: 17

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Ala Phe Ser Trp Val Arg Gln Ala Pro Gly Gln Gly Pro Glu Leu Met
        35                  40                  45

Gly Arg Ile Met Pro Met Phe Asp Ile Ala Ser Tyr Ala Gln Lys Phe
    50                  55                  60

Gln Gly Arg Leu Thr Ile Thr Ala Asp Lys Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Thr Gln Val Ser Gly Asp Ser Tyr Trp Gly Pro Gly Thr Leu Val
            100                 105                 110

Thr Val Ser Ser
        115
```

<210> SEQ ID NO 18
<211> LENGTH: 112
<212> TYPE: PRT
<213> ORGANISM: Homo Sapiens

<400> SEQUENCE: 18

```
Asp Ile Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val His Asn
            20                  25                  30

Asp Gly Asn Thr Tyr Leu Asn Trp Phe His Gln Arg Pro Gly Gln Ser
        35                  40                  45
```

Pro Arg Leu Ile Tyr Lys Val Ser Asn Arg Asp Phe Gly Val Pro
            50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Ser His Trp Pro Leu Thr Phe Gly Gly Gly Thr Lys Val Glu Ile Lys
            100                 105                 110

<210> SEQ ID NO 19
<211> LENGTH: 117
<212> TYPE: PRT
<213> ORGANISM: Homo Sapiens

<400> SEQUENCE: 19

Gln Val Gln Leu Val Gln Ser Gly Ala Glu Val Lys Lys Pro Gly Ser
1               5                   10                  15

Ser Val Lys Val Ala Cys Lys Ala Ser Gly Gly Thr Phe Ser His Ser
                20                  25                  30

Ala Ile Ser Trp Val Arg Gln Ala Pro Gly Gln Gly Leu Glu Trp Ile
            35                  40                  45

Gly Arg Thr Ile Pro Thr Leu Glu Met Ala Ser Tyr Ala Gln Lys Phe
50                  55                  60

Gln Gly Arg Val Thr Ile Ser Ala Asp Lys Ser Thr Arg Thr Gly Tyr
65                  70                  75                  80

Met Glu Leu Arg Asp Leu Arg Ser Glu Asp Thr Ala Val Tyr Tyr Cys
                85                  90                  95

Ser Thr Gln Thr Pro Ser Tyr Thr Asp His Trp Gly Gln Gly Thr Leu
            100                 105                 110

Val Thr Val Ser Ser
            115

<210> SEQ ID NO 20
<211> LENGTH: 112
<212> TYPE: PRT
<213> ORGANISM: Homo Sapiens

<400> SEQUENCE: 20

Asp Val Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val Tyr Arg
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Lys Val Glu Ile Lys
            100                 105                 110

<210> SEQ ID NO 21
<211> LENGTH: 116
<212> TYPE: PRT
<213> ORGANISM: Homo Sapiens

<400> SEQUENCE: 21

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Thr Ser Ser
                20                  25                  30

Gly Met Asn Trp Val Arg Gln Ala Pro Gly Lys Gly Leu Glu Trp Val
            35                  40                  45

Ala Tyr Ile Phe Pro Asn Gly Lys Thr Leu Tyr Pro Glu Ser Val Lys
        50                  55                  60

Gly Arg Phe Ile Ile Thr Arg Asp Asn Ala Glu Lys Ser Leu Phe Leu
65                  70                  75                  80

Glu Met Asn Asn Leu Arg Ala Glu Asp Met Gly Val Tyr Tyr Cys Ala
                85                  90                  95

Ile Asp Leu Asn Trp Gly Ser Gly Tyr Trp Gly Gln Gly Thr Leu Val
            100                 105                 110

Thr Val Ser Ser
            115

<210> SEQ ID NO 22
<211> LENGTH: 110
<212> TYPE: PRT
<213> ORGANISM: Homo Sapiens

<400> SEQUENCE: 22

Ser Tyr Val Leu Thr Gln Pro Pro Ser Val Ser Lys Gly Leu Arg Gln
1               5                   10                  15

Thr Ala Thr Leu Thr Cys Thr Gly Asn Ile Asn Asn Val Gly Asn Val
                20                  25                  30

Gly Ala Thr Trp Leu Gln Gln His Gln Gly His Pro Pro Lys Leu Leu
            35                  40                  45

Ser Asp Arg Asn Asn Arg Pro Ser Gly Ile Ser Glu Arg Phe Ser
        50                  55                  60

Ala Ser Arg Ser Gly Asn Ala Ala Ser Leu Thr Ile Thr Gly Leu Gln
65                  70                  75                  80

Pro Glu Asp Glu Ala Asp Tyr Tyr Cys Ser Ala Trp Asp Thr Ser Leu
                85                  90                  95

Gly Ala Trp Val Phe Gly Gly Gly Thr Lys Leu Thr Val Leu
            100                 105                 110

<210> SEQ ID NO 23
<211> LENGTH: 116
<212> TYPE: PRT
<213> ORGANISM: Homo Sapiens

<400> SEQUENCE: 23

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Lys Lys Ser Tyr Ala Asp Ser Val
        50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Asp Asp Thr Ala Val Tyr Tyr Cys
                85                  90                  95

Ala Thr Ser Ala Gly Gly Gly Tyr Trp Gly Gln Gly Thr Leu Val
            100                 105                 110

Thr Val Ser Ser
        115

<210> SEQ ID NO 24
<211> LENGTH: 110
<212> TYPE: PRT
<213> ORGANISM: Homo Sapiens

<400> SEQUENCE: 24

Gln Ser Val Leu Thr Gln Pro Pro Ser Val Ser Lys Asp Leu Arg Gln
1               5                   10                  15

Thr Ala Thr Leu Thr Cys Thr Gly Asn Ser Asn Asn Val Gly Asp Lys
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Asp Asp Glu Ala Asp Tyr Tyr Cys Ser Ala Trp Asp Ser Ser Leu
                85                  90                  95

Ser Ala Trp Val Phe Gly Gly Gly Thr Lys Leu Thr Val Leu
            100                 105                 110

<210> SEQ ID NO 25
<211> LENGTH: 125
<212> TYPE: PRT
<213> ORGANISM: Homo Sapiens

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Ser Ile Ala Ala Ala Gly Thr Gln Tyr Tyr Tyr Tyr Tyr Met
            100                 105                 110

Asp Val Trp Gly Lys Gly Thr Thr Val Thr Val Ser Ser
        115                 120                 125

<210> SEQ ID NO 26
<211> LENGTH: 107
<212> TYPE: PRT
<213> ORGANISM: Homo Sapiens

<400> SEQUENCE: 26

Asp Ile Gln Leu Thr Gln Ser Pro Ser Ser Leu Ser Ala Ser Val Gly
```

```
1               5                   10                  15
Asp Arg Val Thr Ile Thr Cys Arg Ala Ser Gln Gly Ile Gly Thr Tyr
                20                  25                  30

Leu Ala Trp Phe Gln Gln Lys Pro Gly Lys Val Pro Lys Pro Leu Ile
            35                  40                  45

Tyr Ala Ala Ser Thr Leu Gln Ser Gly Val Pro Ser Arg Phe Ser Gly
        50                  55                  60

Ser Gly Ser Gly Ala Asp Phe Thr Leu Thr Ile Ser Ser Leu Gln Pro
65                  70                  75                  80

Glu Asp Val Ala Thr Tyr Tyr Cys Gln Lys Tyr Asn Ser Val Pro Gln
                85                  90                  95

Thr Phe Gly Gln Gly Thr Lys Val Glu Ile Lys
                100                 105
```

<210> SEQ ID NO 27
<211> LENGTH: 123
<212> TYPE: PRT
<213> ORGANISM: Homo Sapiens

<400> SEQUENCE: 27

```
Gln Val Gln Leu Val Glu Ser Gly Gly Gly Leu Val Gln Pro Gly Arg
1               5                   10                  15

Ser Leu Arg Leu Ser Cys Ile Ile Ser Gly Phe Thr Phe Gly Asp Tyr
                20                  25                  30

Thr Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Gln Tyr Ala Ala
        50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Asp Tyr Gly Asp Phe Pro Trp Tyr Phe Asp Leu
                100                 105                 110

Trp Gly Arg Gly Thr Leu Val Thr Val Ser Ser
            115                 120
```

<210> SEQ ID NO 28
<211> LENGTH: 112
<212> TYPE: PRT
<213> ORGANISM: Homo Sapiens

<400> SEQUENCE: 28

```
Ala Ile Gln Leu Thr Gln Ser Pro Leu Ala Leu Pro Val Pro Leu Gly
1               5                   10                  15

Gln Pro Ala Ser Ile Ser Cys Arg Ala Ser Gln Ser Leu Val Tyr Ser
                20                  25                  30

Asn Gly Asn Thr Tyr Leu Asn Trp Phe Gln Leu Arg Pro Gly Gln Ser
            35                  40                  45

Pro Arg Arg Leu Ile Tyr Lys Val Ser Arg Arg Asp Ser Gly Val Pro
        50                  55                  60

Asp Arg Phe Ser Gly Ser Gly Ser Asp Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Trp Pro Ile Thr Phe Gly Gln Gly Thr Arg Leu Glu Ile Lys
```

-continued

```
                    100                 105                 110
```

<210> SEQ ID NO 29
<211> LENGTH: 116
<212> TYPE: PRT
<213> ORGANISM: Homo Sapiens

<400> SEQUENCE: 29

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Ala Phe Ser Trp Val Arg Gln Ala Pro Gly Gln Gly Pro Glu Leu Met
        35                  40                  45

Gly Arg Ile Met Pro Met Phe Asp Ile Ala Ser Tyr Ala Gln Lys Phe
    50                  55                  60

Gln Gly Arg Leu Thr Ile Thr Ala Asp Lys Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Thr Gln Val Ser Gly Asp Ser Tyr Trp Gly Pro Gly Thr Thr Val
            100                 105                 110

Thr Val Ser Ser
        115
```

<210> SEQ ID NO 30
<211> LENGTH: 112
<212> TYPE: PRT
<213> ORGANISM: Homo Sapiens

<400> SEQUENCE: 30

```
Asp Val Val Met Thr Gln Ser Pro Leu Ser Leu Pro Val Thr Leu Gly
1               5                   10                  15

Gln Pro Ala Ser Ile Ser Cys Arg Ser Thr Gln Ser Leu Val His Ser
            20                  25                  30

Asp Gly Asn Thr Tyr Leu Asn Trp Phe His Gln Arg Pro Gly Gln Ser
        35                  40                  45

Pro Arg Arg Leu Ile Tyr Lys Ile Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Trp Pro Pro Thr Phe Gly Gln Gly Thr Lys Val Glu Ile Lys
            100                 105                 110
```

<210> SEQ ID NO 31
<211> LENGTH: 117
<212> TYPE: PRT
<213> ORGANISM: Homo Sapiens

<400> SEQUENCE: 31

```
Gln Val Gln Leu Val Gln Ser Gly Ala Glu Val Lys Lys Pro Gly Ser
1               5                   10                  15

Ser Val Lys Val Ala Cys Lys Ala Ser Gly Gly Thr Phe Ser His Ser
            20                  25                  30

Ala Ile Ser Trp Val Arg Gln Ala Pro Gly Gln Gly Leu Glu Trp Ile
        35                  40                  45
```

-continued

```
Gly Arg Thr Ile Pro Thr Leu Glu Met Ala Ser Tyr Ala Gln Lys Phe
    50                  55                  60

Gln Gly Arg Val Thr Ile Ser Ala Asp Lys Ser Thr Arg Thr Gly Tyr
65                  70                  75                  80

Met Glu Leu Arg Asp Leu Arg Ser Glu Asp Thr Ala Val Tyr Tyr Cys
                85                  90                  95

Ser Thr Gln Thr Pro Ser Tyr Thr Asp His Trp Gly Gln Gly Thr Leu
            100                 105                 110

Val Thr Val Ser Ser
            115

<210> SEQ ID NO 32
<211> LENGTH: 112
<212> TYPE: PRT
<213> ORGANISM: Homo Sapiens

<400> SEQUENCE: 32

Glu Ile Val Leu Thr Gln Ser Pro Leu Ser Leu Pro Val Thr Leu Gly
1               5                   10                  15

Gln Pro Ala Ser Ile Ser Cys Asn Ser Ser Gln Ser Leu Leu His Arg
            20                  25                  30

Asp Gly His Thr Tyr Leu His Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Lys Phe Ser Gly Ser Gly Ser Gly Thr Glu Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Ala Phe Gly Gly Gly Thr Lys Leu Glu Ile Lys
            100                 105                 110

<210> SEQ ID NO 33
<211> LENGTH: 117
<212> TYPE: PRT
<213> ORGANISM: Homo Sapiens

<400> SEQUENCE: 33

Gln Val Gln Leu Val Gln Ser Gly Ala Glu Val Lys Lys Pro Gly Ser
1               5                   10                  15

Ser Val Lys Val Ala Cys Lys Ala Ser Gly Gly Thr Phe Ser His Ser
            20                  25                  30

Ala Ile Ser Trp Val Arg Gln Ala Pro Gly Gln Gly Leu Glu Trp Ile
        35                  40                  45

Gly Arg Thr Ile Pro Thr Leu Glu Met Ala Ser Tyr Ala Gln Lys Phe
    50                  55                  60

Gln Gly Arg Val Thr Ile Ser Ala Asp Lys Ser Thr Arg Thr Gly Tyr
65                  70                  75                  80

Met Glu Leu Arg Asp Leu Arg Ser Glu Asp Thr Ala Val Tyr Tyr Cys
                85                  90                  95

Ser Thr Gln Thr Pro Ser Tyr Thr Asp His Trp Gly Gln Gly Thr Leu
            100                 105                 110

Val Thr Val Ser Ser
            115

<210> SEQ ID NO 34
```

```
<211> LENGTH: 112
<212> TYPE: PRT
<213> ORGANISM: Homo Sapiens

<400> SEQUENCE: 34

Asp Ile Val Met Thr Gln Thr Pro Leu Ser Leu Pro Val Thr Leu Gly
1               5                   10                  15

Gln Pro Ala Ser Ile Ser Cys Arg Ser Asn Gln Ser Leu Val His Ser
            20                  25                  30

Asp Gly Asn Thr Tyr Leu Tyr Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Val Gly Val Tyr Tyr Cys Met Gln Gly
                85                  90                  95

Thr His Trp Pro Asn Thr Phe Gly Gln Gly Thr Lys Leu Glu Ile Lys
            100                 105                 110

<210> SEQ ID NO 35
<211> LENGTH: 117
<212> TYPE: PRT
<213> ORGANISM: Homo Sapiens

<400> SEQUENCE: 35

Gln Val Gln Leu Val Gln Ser Gly Ala Glu Val Lys Lys Pro Gly Ser
1               5                   10                  15

Ser Val Lys Val Ala Cys Lys Ala Ser Gly Gly Thr Phe Ser His Ser
            20                  25                  30

Ala Ile Ser Trp Val Arg Gln Ala Pro Gly Gln Gly Leu Glu Trp Ile
        35                  40                  45

Gly Arg Thr Ile Pro Thr Leu Glu Met Ala Ser Tyr Ala Gln Lys Phe
    50                  55                  60

Gln Gly Arg Val Thr Ile Ser Ala Asp Lys Ser Thr Arg Thr Gly Tyr
65                  70                  75                  80

Met Glu Leu Arg Asp Leu Arg Ser Glu Asp Thr Ala Val Tyr Tyr Cys
                85                  90                  95

Ser Thr Gln Thr Pro Ser Tyr Asp His Trp Gly Gly Gly Thr Leu
            100                 105                 110

Val Thr Val Ser Ser
        115

<210> SEQ ID NO 36
<211> LENGTH: 112
<212> TYPE: PRT
<213> ORGANISM: Homo Sapiens

<400> SEQUENCE: 36

Asp Ile Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro Leu Thr Phe Gly Gly Gly Thr Lys Val Glu Ile Lys
            100                 105                 110

<210> SEQ ID NO 37
<211> LENGTH: 117
<212> TYPE: PRT
<213> ORGANISM: Homo Sapiens

<400> SEQUENCE: 37

Gln Val Gln Leu Val Gln Ser Gly Ala Glu Val Lys Lys Pro Gly Ser
1               5                   10                  15

Ser Val Lys Val Ala Cys Lys Ala Ser Gly Thr Phe Ser His Ser
            20                  25                  30

Ala Ile Ser Trp Val Arg Gln Ala Pro Gly Gln Gly Leu Glu Trp Ile
        35                  40                  45

Gly Arg Thr Ile Pro Thr Leu Glu Met Ala Ser Tyr Ala Gln Lys Phe
50                  55                  60

Gln Gly Arg Val Thr Ile Ser Ala Asp Lys Ser Thr Arg Thr Gly Tyr
65                  70                  75                  80

Met Glu Leu Arg Asp Leu Arg Ser Glu Asp Thr Ala Val Tyr Tyr Cys
            85                  90                  95

Ser Thr Gln Thr Pro Ser Tyr Thr Asp His Trp Gly Gln Gly Thr Leu
            100                 105                 110

Val Thr Val Ser Ser
        115

<210> SEQ ID NO 38
<211> LENGTH: 112
<212> TYPE: PRT
<213> ORGANISM: Homo Sapiens

<400> SEQUENCE: 38

Asp Val Val Met Thr Gln Ser Pro Val Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Phe Asn Trp Phe Gln Gln Arg Pro Gly Gln Ser
        35                  40                  45

Pro Arg Arg Leu Ile Tyr Lys Val Ser Asn Arg Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro Ile Thr Phe Gly Gln Gly Thr Arg Leu Glu Ile Lys
            100                 105                 110

<210> SEQ ID NO 39
<211> LENGTH: 117
<212> TYPE: PRT
<213> ORGANISM: Homo Sapiens

<400> SEQUENCE: 39

Gln Val Gln Leu Val Gln Ser Gly Ala Glu Val Lys Lys Pro Gly Ser

```
1               5                   10                  15
Ser Val Lys Val Ala Cys Lys Ala Ser Gly Gly Thr Phe Ser His Ser
            20                  25                  30

Ala Ile Ser Trp Val Arg Gln Ala Pro Gly Gln Gly Leu Glu Trp Ile
            35                  40                  45

Gly Arg Thr Ile Pro Thr Leu Glu Met Ala Ser Tyr Ala Gln Lys Phe
            50                  55                  60

Gln Gly Arg Val Thr Ile Ser Ala Asp Lys Ser Thr Arg Thr Gly Tyr
65                  70                  75                  80

Met Glu Leu Arg Asp Leu Arg Ser Glu Asp Thr Ala Val Tyr Tyr Cys
                85                  90                  95

Ser Thr Gln Thr Pro Ser Tyr Thr Asp His Trp Gly Gln Gly Thr Leu
            100                 105                 110

Val Thr Val Ser Ser
            115

<210> SEQ ID NO 40
<211> LENGTH: 112
<212> TYPE: PRT
<213> ORGANISM: Homo Sapiens

<400> SEQUENCE: 40

Asp Ile Val Met Thr Gln Thr Pro Leu Ser Leu Pro Val Thr Leu Gly
1               5                   10                  15

Gln Pro Ala Ala Ile Ser Cys Arg Ser Ser Gln Ser Leu Val Tyr Ser
            20                  25                  30

Asp Gly Asn Thr Tyr Leu Asn Trp Phe His Gln Arg Pro Gly Gln Ser
            35                  40                  45

Pro Arg Arg Leu Ile Tyr Lys Val Ser Asn Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Leu Glu Ile Lys
            100                 105                 110

<210> SEQ ID NO 41
<211> LENGTH: 117
<212> TYPE: PRT
<213> ORGANISM: Homo Sapiens

<400> SEQUENCE: 41

Gln Val Gln Leu Val Gln Ser Gly Ala Glu Val Lys Lys Pro Gly Ser
1               5                   10                  15

Ser Val Lys Val Ala Cys Lys Ala Ser Gly Gly Thr Phe Ser His Ser
            20                  25                  30

Ala Ile Ser Trp Val Arg Gln Ala Pro Gly Gln Gly Leu Glu Trp Ile
            35                  40                  45

Gly Arg Thr Ile Pro Thr Leu Glu Met Ala Ser Tyr Ala Gln Lys Phe
            50                  55                  60

Gln Gly Arg Val Thr Ile Ser Ala Asp Lys Ser Thr Arg Thr Gly Tyr
65                  70                  75                  80

Met Glu Leu Arg Asp Leu Arg Ser Glu Asp Thr Ala Val Tyr Tyr Cys
                85                  90                  95

Ser Thr Gln Thr Pro Ser Tyr Thr Asp His Trp Gly Gln Gly Thr Leu
```

-continued

```
            100                 105                 110
Val Thr Val Ser Ser
            115

<210> SEQ ID NO 42
<211> LENGTH: 112
<212> TYPE: PRT
<213> ORGANISM: Homo Sapiens

<400> SEQUENCE: 42

Asp Ile Val Met Thr Gln Ser Pro Leu Ser Leu Pro Val Thr Leu Gly
1               5                   10                  15

Gln Pro Ala Ser Ile Ser Cys Arg Ser Ser His Thr Leu Val His Ser
            20                  25                  30

Asp Gly Thr Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Val Glu Ile Lys
            100                 105                 110
```